United States Patent
Hotzel et al.

(10) Patent No.: US 10,308,944 B2
(45) Date of Patent: Jun. 4, 2019

(54) POLYPEPTIDE EXPRESSION SYSTEMS

(71) Applicant: Genentech, Inc., South San Francisco, CA (US)

(72) Inventors: Isidro Hotzel, Brisbane, CA (US); Yonglei Shang, Millbrae, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 14/790,818

(22) Filed: Jul. 2, 2015

(65) Prior Publication Data

US 2016/0002642 A1  Jan. 7, 2016

Related U.S. Application Data

(60) Provisional application No. 62/080,698, filed on Nov. 17, 2014, provisional application No. 62/020,838, filed on Jul. 3, 2014.

(51) Int. Cl.
*C07K 16/00* (2006.01)
*C12N 15/63* (2006.01)
*C12P 21/00* (2006.01)

(52) U.S. Cl.
CPC ............ *C12N 15/63* (2013.01); *C07K 16/005* (2013.01); *C12P 21/00* (2013.01); *C07K 2317/10* (2013.01); *C07K 2317/52* (2013.01); *C07K 2317/55* (2013.01); *C07K 2317/60* (2013.01); *C07K 2317/62* (2013.01); *C07K 2317/64* (2013.01)

(58) Field of Classification Search
None
See application file for complete search history.

(56) References Cited

U.S. PATENT DOCUMENTS

| | | | | |
|---|---|---|---|---|
| 6,150,141 A * | 11/2000 | Jarrell | ..................... | C07K 16/00 435/91.1 |
| 7,112,439 B2 * | 9/2006 | Johnson | ................. | C07K 16/00 435/252.3 |
| 2006/0246422 A1 * | 11/2006 | Mitchell | .............. | C12N 9/2471 435/5 |
| 2006/0246542 A1 * | 11/2006 | Simmons | ............... | C07K 16/00 435/69.1 |
| 2007/0224664 A1 * | 9/2007 | Simmons | ............... | C07K 16/00 435/69.6 |
| 2010/0120634 A1 * | 5/2010 | Hufton | ............... | C12N 15/1037 506/18 |
| 2014/0011981 A1 | 1/2014 | Tesar et al. | | |
| 2014/0045216 A1 * | 2/2014 | Do | ......................... | C07K 14/47 435/69.7 |

FOREIGN PATENT DOCUMENTS

| | | | |
|---|---|---|---|
| WO | WO-0192291 A2 * | 12/2001 | ............. C07K 16/00 |
| WO | WO-2004/063343 A2 | 7/2004 | |
| WO | WO-2006/083331 A2 | 8/2006 | |

OTHER PUBLICATIONS

Invitrogen's pcDNA3.1 User Manual, published Nov. 10, 2010, 23 pages.*
Iwasaki et al. (2009) Trans-splicing as a novel method to rapidly produce antibody fusion proteins. Biochemical and Biophysical Research Communications, 384:316-321.*
Shields et al. (2009) Treatment of Collagen-Induced Arthritis with Lentiviral BIP Improves Clinical Parameters of Disease. Annual Rheum Dis, 69(Suppl 2):A56-A57.*
Xiao et al. (2009) Splice site strength-dependent activity and genetic buffering by poly-G runs. Nature Structural & Molecular Biology, 16(10):1094-1100, and online methods, 1 page.*
Tesar et al. (2013) A dual host vector for Fab phage display and expression of native IgG in mammalian cells. Protein Engineering, Design & Selection, 26(10):655-662.*
Yang et al. (2009) Mutated Polyadenylation Signals for Controlling Expression Levels of Multiple Genes in Mammalian Cells. Biotechnology and Bioengineering, 102(4):1152-1160.*
Fath et al. (2011) Multiparameter RNA and Codon Optimization: A Standardized Tool to Assess and Enhance Autologous Mammalian Gene Expression. PLoS ONE, 6(3):e17596, pp. 1-14 (Year: 2011).*
Database Accession No. B1A4G6, retrieved Jun. 29, 2016 (7 pages).
Database Accession No. P15703, retrieved Nov. 5, 2013 (7 pages).
Database Accession No. P20029, retrieved Nov. 5, 2013 (10 pages).
Database Accession No. Q9BLZ2, retrieved Nov. 5, 2013 (2 pages).
Hall et al., "Eukaryotic and prokaryotic signal peptides direct secretion of a bacterial endoglucanase by mammalian cells," J Biol Chem. 265(32):19996-9 (1990).
Hastings et al., "A purine-rich intronic element enhances alternative splicing of thyroid hormone receptor mRNA," RNA. 7(6):859-74 (2001).
Humphreys et al., "High-level periplasmic expression in *Escherichia coli* using a eukaryotic signal peptide: importance of codon usage at the 5' end of the coding sequence," Protein Expr Purif. 20(2):252-64 (2000).
Kim et al., "Translation levels control multi-spanning membrane protein expression," PLoS One. 7(4):e35844 (2012).
Konarska et al., "Trans splicing of mRNA precursors in vitro," Cell. 42(1):165-71 (1985).
Lee et al., "Bivalent antibody phage display mimics natural immunoglobulin," J Immunol Methods. 284(1-2):119-32 (2004).
Martinez-Contreras et al., "Intronic binding sites for hnRNP A/B and hnRNP F/H proteins stimulate pre-mRNA splicing," PLoS Biol. 4(2):e21 (2006) (14 pages).
McCafferty et al., "Phage antibodies: filamentous phage displaying antibody variable domains," Nature. 348(6301):552-4 (1990).
Monjaret et al., "Cis-splicing and translation of the pre-transsplicing molecule combine with efficiency in spliceosome-mediated RNA trans-splicing," Mol Ther. 22(6):1176-87 (2014).
Quinlan et al., "Direct expression and validation of phage-selected peptide variants in mammalian cells," J Biol Chem. 288(26):18803-10 (2013).

(Continued)

*Primary Examiner* — Neil P Hammell
(74) *Attorney, Agent, or Firm* — Clark & Elbing LLP; Karen L. Elbing

(57) ABSTRACT

The present invention relates to polypeptide expression systems and methods of using the same.

47 Claims, 16 Drawing Sheets

Specification includes a Sequence Listing.

(56) References Cited

OTHER PUBLICATIONS

Pergolizzi et al., "Genetic medicine at the RNA level: modifications of the genetic repertoire for therapeutic purposes by pre-mRNA trans-splicing," C R Biol. 327(8):695-709 (2004).

Puttaraju et al., "Spliceosome-mediated RNA trans-splicing as a tool for gene therapy," Nat Biotechnol. 17(3):246-52 (1999).

Schlesinger et al., "In-cell generation of antibody single-chain Fv transcripts by targeted RNA trans-splicing," J Immunol Methods. 282(1-2):175-86 (2003).

Shang et al., "Modular protein expression by RNA trans-splicing enables flexible expression of antibody formats in mammalian cells from a dual-host phage display vector," Protein Eng Des Sel. 28(10):437-44 (2015) (8 pages).

Sidhu, "Phage display in pharmaceutical biotechnology," Curr Opin Biotechnol. 11(6):610-6 (2000).

Smith, "Filamentous fusion phage: novel expression vectors that display cloned antigens on the virion surface," Science. 228(4705):1315-7 (1985).

Solnick, "Trans splicing of mRNA precursors," Cell. 42(1):157-64 (1985).

Tesar et al., "A dual host vector for Fab phage display and expression of native IgG in mammalian cells," Protein Eng Des Sel. 26(10):655-62 (2013).

Wang et al., "Intronic splicing enhancers, cognate splicing factors and context-dependent regulation rules," Nat Struct Mol Biol. 19(10):1044-52 (2012).

Xiao et al., "Splice site strength-dependent activity and genetic buffering by poly-G runs," Nat Struct Mol Biol. 16(10):1094-100 (2009).

Invitation to Pay Additional Fees for International Application No. PCT/US2015/039086, dated Sep. 25, 2015 (9 pages).

International Search Report and Written Opinion for International Patent Application No. PCT/US2015/039086, dated Dec. 14, 2015 (20 pages).

International Preliminary Report on Patentability for International Application No. PCT/US2015/039086, dated Jan. 3, 2017 (10 pages).

* cited by examiner

FIG. 2

| FIG. 2A |
| FIG. 2B |

FIG. 2A

```
                                                5'ss <         CMVie intron A fragment        ><phoA
GCCACCATGA TGAAATTTAC CGTGGTGGCG GCGGCGCTGC TGCTGCTGGG CGGTAAGTAC CGCCTATAGA GTCTATAGGC CCACCCCCTT GGCTTACGTA
 M  M  K  F  T  V  V  A  A  A  L  L  L  L  L  L (SEQ. ID No: 3)
^Light Chain signal sequence (BiP)

AAGAAGTTAT TGAAGCATCC TCGTCAGTAA AAAGTTAATC TTTTCAACAG CTGTCATAAA GTTGTCACGG CCGAGACTTA TAGTCGCTTT GTTTTTATTT

TTTTATGTAT TTGTAACTAG TACGCAAGTT CACGTAAAAA GGGTATGTAG AGGTTGAGGT GATTTTATGA AAAGAATAT CGCATTTCTT CTTGCATCTA
                                                                         M  K  N  I  A  F  L  L  A  S  M
                                                                      < Modified stII signal sequence
Polypyrimidine tract  3'ss
TGTTCCTTTT TTCTCTTTTC ACAGCCGTAC GCGCAGATAT CCAGATGACC CAGTCCCCGA GCTCCCCTGT CGCCTCTGTG GGCGATAGGG TCACCATCAC
                                A  D  I  Q  M  T  Q  S  P  S  S  L  S  A  S  V  G  D  R  V  T  I  T
                                                                                      (SEQ. ID No: 2)
  F  L  F  S  L  S  T  A  V  R
                                < Light chain
                                                                                      (SEQ. ID No: 9)

5'ss <         CMVie intron A fragment       ><phoA
GCCACCATGG GATGGTCATG TATCATCCTT TTTCTAGTAG CAACTGCAAC AGGTAAGTAC CGCCTATAGA GTCTATAGGC CCACCCCCTT GGCTTACGTA
 M  G  W  S  C  I  I  L  F  L  V  A  T  A  T (SEQ. ID No: 19)
^Heavy chain signal sequence (Ig)

AAGAAGTTAT TGAAGCATCC TCGTCAGTAA AAAGTTAATC TTTTCAACAG CTGTCATAAA GTTGTCACGG CCGAGACTTA TAGTCGCTTT GTTTTTATTT

TTTTATCATC GTGGCCCTAG TACGCAAATT CACGTAACTAG AGGTTGAGGT GATTTTATGA AAAAGAATAT CGCATTTCTT CTTGCATCTA
                                                                         M  K  K  N  I  A  F  L  L  A  S  M
                                                                      < Modified stII signal sequence
```

Polypyrimidine tract 3'ss
TGTTCCTTTT TTCTCTTTCC ACAGCGGTCC GCGCAGAAGT TCAGCTGGTG GAGTCTGGGG GTGGCCTGGT GCAGCCAGGG GGCTCACTCC GTTGTCCTG
                                                                                                (SEQ. ID No: 10)
          F  L  F  S  L  S  T  A  V  R  A  E  V  Q  L  V  E  S  G  G  G  L  V  Q  P  G  G  S  L  R  L  S  C
          < Heavy chain                                                                         (SEQ. ID No: 20)
                         5' ss                                                           < dsRNA
CACAAGCCCA GCAACACCAA GGTCGACAAG AAAGTAGGTA AGAAATCTTG TGACAAAACT CACACAATGCG GCCGGCCCTC TGGTTCCGGT GATTTTGATT
  H  K  P  S  N  T  K  V  D  K  K  V  G  K        K  S  C  D  K  T  H  T  C  G   R  P  S  G  G  D  F  D  Y
CH1                                                                                  < Linker >< C-terminal P3 (cP3)
ATGAAAAGAT GGCAAACGCT AATAGGGGG CTATGACCGA AAATGCCGAT GAAAACGCGC TACAGTCTGA CGCTAAAGGC AAACTTGATT CTGTCGCTAC
  E  K  M  A  N  A  N  K  G  A  M  T  E  N  A  D  E  N  A  L  Q  S  D  A  K  G  K  L  D  S  V  A  T
TGATTACGGT GCTGCTATCG ATGGTTTCAT TGGTGACGTT TCCGGCCTTG CTAATGGTAA TGGTGCTACT GGTGATTTTG CTGGCTCTAA TTCCCAAATG
  D  Y  G  A  A  I  D  G  F  I  G  D  V  S  G  L  A  N  G  N  G  A  T  G  D  F  A  G  S  N  S  Q  M
GCTCAAGTCG GTGACGGTGA TAATTGAATT TTAATTCACCT TTAATGAATA ATTTCCGTCA ATATTTACCT TCTTTGCCGT TCTTTGCGTT TGTGTCTTTA
  A  Q  V  G  D  G  D  N  S  P  L  M  N  N  F  R  Q  Y  L  P  S  L  P  Q  S  V  E  C  R  P  F  V  F  S
                                     AATAAA
GCGCTGGTAA ACCATATGAA TTTTCTATTG ATTGTGACAA GATTAACTTA TTCCGTGGTG TCTTTGCGTT TCTTTTATAT GTTGCCACCT TTATGTATGT
  A  G  K  P  Y  E  F  S  I  D  C  D  K  I  N  L  F  R  G  V  F  A  F  L  L  Y  V  A  T  F  M  Y  V
ATTTTCTACG TTTGCTAACA TACTGCGTAA TAAGGAGTCT TAACCGTGGG GTGAACGCTC GGTGCCGCC GGGCGTTTTT TATGTTCTTT TGAGGATCC
  F  S  T  F  A  N  I  L  R  N  K  E  S  *  (SEQ. ID No: 22)                                    (SEQ. ID No: 21)

FIG. 2B

TATA box
 +1 RNA site
GTCTATATAA GCAGAGCTCG TTTAGTGAAC CGTCAGATCG CCTGGAGACG CCATCCACGC TGTTTTGACC TCCATAGAAG ACACCGGGAC CGATCCAGCC Antisense gene III sequence
TCCGGGCCCG GGAACGGTGC ATTGGAACGC GGATTCCCCG TGCCAAGAGT GACGAACGTC ACCAATGAAA CCATCGATAG CAGCACCGTA ATCAGTAGCG ACAGAATCAA GTTTGCCTTT AGCGTCAGAC TGTAGGCGT TTTCATCGGC ATAGCCCCCT TATTAGCGTT TGCCATCTTT TCATAATCAA BP
AATCCCACCC CCTTGGCTTC GTTAGTAGAC TAGATCTAAT CTACTCTACT AACCGCCTAT AGAGTCTATA GGCCCACCCC CTTGGCTTTA CTGACACACG
   Polypyrimidine tract    3' ss
AATTCCCTCTT TCCCTTTCTC TCCACAGAGC CCAAATCTTG TGACAAAACT CACACATGCC CACCGTGCCC AGCACCTGAA CTCCTGGGCG GACCGTCAGT
                              (E) P   K   S   C   D   K   T   H   T   C   P   P   C   P   A   P   E   L   L   G   G   P   S   V
                               V                                                  > < CH2
                                                      Hinge CTTCCTCTTC CCCCCAAAACC CAAGGACAC CCTCATGAT TCCCGGACCC CTGAGGTCAC ATGCGTGGTG GTGGACGTGA GCCACGAAGA CCCTGAGGTC
  F   L   F   P   P   K   P   K   D   T   L   M   I   S   R   T   P   E   V   T   C   V   V   V   D   V   S   H   E   D   P   E   V
                                                                                                                        (SEQ. ID No: 23)
                                                                                                                        (SEQ. ID No: 24)

| FIG. 5A |
|---------|
| FIG. 5B |

FIG. 5A

```
                                                                                              5' ss                                              <PhoA
GCCACCATGA TGAAATTTAC CGTGGTGGCG GCGGGCTGC TGCTGCTGGG GCGGGCTGC CGCTATAGGA GTCTATAGGA CCACCCCCTT GGCTTACGTA
         M  M  K  F  T  V  V  A  A  A  L  L  L  L  G (SEQ. ID No: 25)
         <Light Chain signal sequence (from murine BiP gene)

AAGAAGTTAT TGAAGCATCC TCGTCAGTAA AAAGTTAATC TTTTCAACAG CTGTCATAAA GTTGTCACGG CCGAGACTTA TAGTCGCTTT GTTTTTATTT

TTTTATGTAT TTGTAACTAG TACGCAAGTT CACGTAAAAA GGGTATGTAG GATTTTATGA AAAAGAATAT CGCATTTCTT CTTGCATCTA
                                                                  M  K  K  N  I  A  F  L  L  A  S  M
                                                                  <Modified stII signal sequence G   PPT  A  G  T   3'ss BsiWI
TGTTCCTTTT TTCTCTTTCC ACAGCCGTAC GCGCAGATAT CCAGATGACC CAGTCCCCGA GCTCCCTGTC CGCCTCTGTG GGCGATAGGG TCACCATCAC
                                                                                                    (SEQ. ID No: 2)
F  L  F  S  L  S     T(A) V  R  A  D  I  Q  M  T  Q  S  P  S  S  L  S  A  S  V  G  D  R  V  T  I  T
V     I  A                     <Light chain variable region                                    (SEQ. ID No: 9)

[Light chain, SV40 poly(A), CMV promoter]

5' ss                                              <PhoA
GCCACCATGG GATGGTCATG TATCATCCCT TTTCTTGGTA CAACTGCAAC AGGTAAGTAC CGCCTATAGA GTCTATAGGC CCACCCCCTT GGCTTACGTA
         M  G  W  S  C  I  I  L  F  L  V  A  T  A  T (SEQ. ID No: 19)
         <Heavy chain signal sequence (from murine VH gene)

AAGAAGTTAT TGAAGCATCC TCGTCAGTAA AAAGTTAATC TTTTCAACAG CTGTCATAAA GTTGTCACGG CCGAGACTTA TAGTCGCTTT GTTTTTATTT

TTTTATCATC GTGGCCCTAG TACGCAAATT CACGTAAAAA GGGTAACTAG AGGTTGAGGT GATTTTATGA AAAAGAATGA CGCATTTCTT CTTGCATCTA
                                                                              M  K  K  N  I  A  F  L  L  A  S  M
                                                                              <Modified stII signal sequence
```

```
G   PPT  A  G  T  3'ss RsrII
TGTTCCTTTT TTCTCTTTCC ACAGCGGTCC GCGCAGAAGT TCAGCTGGTG GAGTCTGGGG GTGGCCTGGT GCAGCCAGGG GGCTCACTCC GTTTGTCCTG
F  L F   S  L S    T(A) V  R    A  E  V    Q  L  V    E  S  G  G    G  L  V    Q  P  G    G  S  L  R    (SEQ. ID No: 10)
      V              I  A                                                                               L  S  C    (SEQ. ID No: 20)

< Heavy chain variable region

...CH1                                              :[Intervening VH and CH1 sequences]                 5'ss
GTGGTGACCG TGCCCTCCAG CAGCTTGGGC ACCCAGACCT ACATCTGCAA CGTGAATCAC AAGCCCAGCA ACACCAAGGT CGACAAGAAA GTAGGTAAGA
V  V  T  V  P  S  S    S  L  G    T  Q  T    Y  I  C  N    V  N  H    K  P  S  N    T  K  V    D  K  K    V  G  K  K <Upper hinge (in E.coli)><  ISR/Purine-rich  >    < M13 Gene III
AATCTGTGA CAAAACTCAC ACATGCCGGG GGGGGAGCGG GAGCGGGAGC GGGGAT TTTGATTATG AAAAGATGGC AAACGCTAAT AAGGGGGCTA TGACCGAAAA
S  C  D   K  T  H   T  C  G  G   G  G  S  G   S  G  D   F  D  Y  E    K  M  A    N  A  N    K  G  A  M    T  E  N
               < LINKER >< C-terminal P3 (cP3)

TGCCGATGAA AACGCGCTAC AGTCTGACGC TAAAGCCAAA CTTGATTCTG TCGCTACTGA TTACGGTGCT GCTATCGATG GTTTCATTGG TGACGTTTCC
A  D  E    N  A  L  Q    S  D  A    K  G  K    L  D  S  V    A  T  D    Y  G  A    A  I  D  G    F  I  G    D  V  S

GGCCTTGCTA ATGGTAATGG TGCTACTGGT GATTTTGCTG GCTCTAATTC CAATGGGGCT ACGGTGAATA TCCCTCTAGA TGGTGATAAC TCACCTTTTA ATGAATAATT
G  L  A  N    G  N  G    A  T  G    D  F  A  G    S  N  S    N  G  A    T  V  N    S  P  L    M  N  N  F

TCCCTCAATA TTTACCTTCC CTCCCTCAAT CGGTTGAATG TCGCCCTTTT GTCTTTAGCG CTGGTAAACC ATATGAATTT TCTATTGATT GTGACAAGAT ATT
R  Q  Y    L  P  S  L    P  Q  S    V  E  C    R  P  F    V  F  S  A    G  K  P    Y  E  F    S  I  D  C    D  K  I

AAA
CAACTTATTC CGTGGTGTCT TTGGCGTTTCT TTTATATGTT GCCACCTTTA TGTATGTATT TTCTACGTTT GCTAACATAC TGCGTAATAA GGAGCTTAA    (SEQ. ID No: 26)
N  L  F    R  G  V  F    A  F  L    L  Y  V    A  T  F  M    Y  V  F    S  T  F    A  N  I  L    R  N  K    E  S  *    (SEQ. ID No: 27)

FIG. 5B
```

```
TATA box                    +1 RNA site
GTCTATATAA GCAGAGCTCG TTTAGTGAAC CGTCAGATCG CCTGGAGACG CCATCCACGC TGTTTTGACC TCCATAGAAG ACACCGGGAC CGATCCCAGCC
                                                                    Antisense gene III sequence
TCCGCGGCCG GGAACGGTGC ATTGGAACCC GGATTCCCCG TGCCAAGAGT GACGAACGTC ACCAATGAAA CCATCGATAG CAGCACCGTA ATCAGTAGCG
ACAGAATCAA GTTTGCCTTT AGCGTCAGAC TGTAGCGCGT TTTCATCGGC ATTTTCGGTC ATAGCCCCCT TATTAGCGTT TGCCATCTTT TCATAATCAA
                                                      < ISE >
AATCCCACCC CCTTGGCTTC GTTAGTAGAC TAGATCTAAT CTACTCTACT AGGAAGTGAC ACCGCCTATA GAGTCTATAG GCCCACCCCC TTGGCTTTAC
BP         Polypyrimidine tract       3'ss
TGACACACGA ATTCCTCTTT CCCTTTCTCT CCACAGAGCC CAAATTCTTGT GACAAAACTC ACCGTGCCCA GCACCTGAAC TCCTGGGCGG
                                   (E) P  K   S   C   D   K   T   H   T   C   P   P   C   P   A   P   E   L   L   G   G
                                     <                         Hinge                          >  <    CH2

ACCGTCAGTC TTCCTCTTCC CCCCAAAACC CAAGGACACC CTCATGATCT CCCGGACCCC TGAGGTCACA TGCGTGGTGG TGGACGTGAG CCACGAAGAC
                                                                                                     (SEQ. ID No: 28)
 P   S   V   F   L   F   P   P   K   P   K   D   T   L   M   I   S   R   T   P   E   V   T   C   V   V   V   D   V   S   H   E   D
                                                                                                     (SEQ. ID No: 29)
```

```
TATA box                    +1 RNA site
GTCTATATAA GCAGAGCTCG TTTAGTGAAC CGTCAGATCG CCTGGAGACG TGTTTTGACC TCCATAGAAG ACACCGGGAC CGATCCAGCC Antisense gene III sequence for dsRNA formation
TCCGCGGGCG GGAACGGTGC ATTGGAACGC GGATTCCCCG TGCCAAGAGT GACGAACGTC ACCAATGAAA CCATCGATAG CAGCACCGTA ATCAGTAGCG ACAGAATCAA GTTTGCCTTT AGCGTCAGAC TGTAGCGCGT TTTCATCGGC ATTTTCGGTC ATAGCCCCCT TATTAGCGTT TGCCATCTTT TCATAATCAA ISE
AATCCCACCC CCTTGGCTTC GTTAGTAGAC TAGATCTAAT CTACTCTACT AGGGGGGGGG ACCGCCTATA GAGTCTATAG GCCCACCCCC TTGGCTTTAC BP       Polypyrimidine tract         3'ss
TGACACACGA ATCCTCCTT CCCTTCTCT CCACAGAGCC CAAATCTTGT GACAAAACTC ACACAGATTA TAAGGACGAT GACGATAAAT GAGTGCGACG
                                                                                                  (SEQ ID No: 30)
           E   P   K   S   C   D   K   T   H   T   D   Y   K   D   D   D   D   K   *
           <        Upper Hinge      >   <     Flag tag         >            (SEQ ID No: 31)
```

POLYPEPTIDE EXPRESSION SYSTEMS

SEQUENCE LISTING

The instant application contains a Sequence Listing which has been submitted electronically in ASCII format and is hereby incorporated by reference in its entirety. Said ASCII copy, created on Jun. 25, 2015 is named P05833-US-2_SL.txt and is 24,421 bytes in size.

FIELD OF THE INVENTION

The present invention relates to polypeptide expression systems for the modular expression and production of polypeptides.

BACKGROUND

Recombinant polypeptides are sometimes expressed as fusions of individual domains or tags for functional or purification purposes. Recombinant DNA methods are traditionally used to join the sequences encoding each module, requiring a different construct for each combination. This poses a challenge to technologies involving expression of large protein collections composed of recurring modules joined in different combinations, as the number of constructs increases geometrically as a function of the number of modules used.

Although high-throughput systems for subcloning can handle large number of inserts in parallel, they are usually resource-intensive and generate a large number of constructs that are ultimately not necessary after initial characterization steps. Thus, there is an unmet need in the field for the development of a polypeptide expression system that allows for the modular expression and production of recombinant polypeptides.

SUMMARY

The present invention relates to polypeptide expression systems for the modular expression and production of polypeptides.

In one aspect, the invention features a polypeptide expression system comprising a first nucleic acid molecule and a second nucleic acid molecule, wherein: (a) the first nucleic acid molecule comprises a first expression cassette comprising the following components: (i) a first eukaryotic promoter ($P1_{Euk1}$), (ii) a first polypeptide-encoding sequence ($PES1_1$), (iii) a first 5' splice site ($5'ss1_1$), and (iv) a hybridizing sequence (HS1), wherein the components are operably linked to each other in a 5'-to-3' direction as $P1_{Euk1}$-$PES1_1$-$5'ss1_1$-HS1; and (b) the second nucleic acid molecule comprises the following components: (i) a eukaryotic promoter ($P2_{Euk}$), (ii) a hybridizing sequence capable of hybridizing to HS1 (HS2), (iii) a 3' splice site (3'ss2), (iv) a polypeptide-encoding sequence (PES2), and (v) a polyadenylation site (pA2), wherein the components are operably linked to each other in a 5'-to-3' direction as $P2_{Euk}$-HS2-3'ss2-PES2-pA2. In some embodiments, the $P1_{Euk1}$ is a cytomegalovirus (CMV) promoter or a simian virus 40 (SV40) promoter. In some embodiments, the $P2_{Euk}$ is a CMV promoter or an SV40 promoter. In some embodiments, the first expression cassette further comprises a first nucleic acid sequence encoding a eukaryotic signal sequence ($ESS1_1$), wherein the $ESS1_1$ is positioned between the $P1_{Euk1}$ and the $PES1_1$. In some embodiments, the $ESS1_1$ is derived from the variable heavy chain (VH) gene.

In some embodiments, the first expression cassette further comprises an excisable prokaryotic promoter module ($ePPM_1$) comprising the following components: (i) a 5' splice site ($5'ss1_2$), (ii) a prokaryotic promoter ($P1_{Prok1}$), and (iii) a 3' splice site ($3'ss1_1$), wherein the components are operably linked to each other in a 5'-to-3' direction as $5'ss1_2$-$P1_{Prok1}$-$3'ss1_1$, and wherein the $ePPM_1$ is positioned between the $P1_{Euk1}$ and the $PES1_1$. In some embodiments, the $P1_{Prok1}$ is a selected from the group consisting of a PhoA promoter, a Tac promoter, a Lac, and a Tphac promoter. In some embodiments, the $ePPM_1$ further comprises a first nucleic acid sequence encoding a prokaryotic signal sequence ($PSS1_1$). In some embodiments, the $PSS1_1$ is derived from the heat-stable enterotoxin II (stII) gene. In some embodiments, the polypeptide expression system further comprises a polypyrimidine tract positioned between the $PSS1_1$ and the $3'ss1_1$ ($PPT1_1$). In some embodiments, the $PPT1_1$ comprises the nucleic acid sequence of TTCCTTTTTCTCTTTCC (SEQ ID NO: 1). In some embodiments, the $PES1_1$ does not comprise a cryptic 5' splice site. In some embodiments, the HS1 is a gene encoding all or a portion of a coat protein or an adaptor protein. In some embodiments, the coat protein is selected from the group consisting of pI, pII, pIII, pIV, pV, pVI, pVII, pVIII, pIX and pX of bacteriophage M13, f1, or fd. In some embodiments, the coat protein is the pIII protein of bacteriophage M13. In some embodiments, the pIII fragment comprises amino acid residues 267-421 of the pIII protein or amino acid residues 262-418 of the pIII protein. In some embodiments, the adaptor protein is a leucine zipper. In some embodiments, the leucine zipper comprises the amino acid sequence of SEQ ID NO: 4 or 5.

In some embodiments, the first nucleic acid molecule further comprises a second expression cassette comprising a second eukaryotic promoter ($P1_{Euk2}$), (ii) a second polypeptide-encoding sequence ($PES1_2$), and (iii) a polyadenylation site (pA1), wherein the components are operably linked to each other in a 5'-to-3' direction as $P1_{Euk2}$-$PES1_2$-pA1. In some embodiments, the $P1_{Euk2}$ is a CMV promoter or an SV40 promoter. In some embodiments, the second expression cassette further comprises a second nucleic acid sequence encoding a eukaryotic signal sequence ($ESS1_2$). In some embodiments, the $ESS1_2$ is derived from the murine binding immunoglobulin protein (mBiP) gene. In some embodiments, the $ESS1_2$ comprises the nucleic acid sequence of ATG AAN TTN ACN GTN GTN GCN GCN GCN CTN CTN CTN CTN GGN, wherein N is A, T, C, or G (SEQ ID NO: 6).

In some embodiments, the second expression cassette further comprises an excisable prokaryotic promoter module ($ePPM_2$) comprising the following components: (i) a 5' splice site ($5'ss1_3$), (ii) a prokaryotic promoter ($P1_{Prok2}$), and (iii) a 3' splice site ($3'ss1_2$), wherein the components are operably linked to each other in a 5'-to-3' direction as $5'ss1_3$-$P1_{Prok2}$-$3'ss1_2$, and wherein the $ePPM_2$ is positioned between the $P1_{Euk2}$ and the $PES1_2$. In some embodiments, the $P1_{Prok2}$ is a selected from the group consisting of a PhoA promoter, a Tac promoter, and a Lac promoter. In some embodiments, the $ePPM_2$ further comprises a nucleic acid sequence encoding a prokaryotic signal sequence ($PSS1_2$). In some embodiments, the $PSS1_2$ is derived from the heat-stable enterotoxin II (stII) gene. In some embodiments, the polypeptide expression system further comprises a polypyrimidine tract positioned between the $PSS1_2$ and the $3'ss1_2$ ($PPT1_2$). In some embodiments, the $PPT1_2$ comprises the nucleic acid sequence of TTCCTTTTTCTCTTTCC (SEQ ID NO: 1). In some embodiments, the second expression cassette is positioned 5' to the first expression cassette. In some embodiments, the polypeptide expression system further comprises an intronic splice enhancer (ISE) positioned between the 5'ss1$_1$ and the HS1 (ISE1). In some embodiments, the ISE1 comprises a G-run comprising three or more consecutive guanine residues. In some embodiments, the ISE1 comprises a G-run comprising nine consecutive guanine residues. In some embodiments, the polypeptide expression system further comprises a polypyrimidine tract positioned between the HS2 and the 3'ss2 (PPT2). In some embodiments, the PPT2 comprises the nucleic acid sequence of TTCCTCTTTCCCTTTCTCTCC (SEQ ID NO: 7). In some embodiments, the polypeptide expression system further comprises an ISE positioned between the HS2 and the 3'ss2 (ISE2). In some embodiments, the ISE2 comprises a G-run comprising three or more consecutive guanine residues. In some embodiments, the ISE2 comprises a G-run comprising nine consecutive guanine residues. In some embodiments, the 5'ss1$_1$ comprises the nucleic acid sequence of GTAAGA (SEQ ID NO: 8).

In some embodiments, expression by a eukaryotic promoter occurs in a mammalian cell. In some embodiments, the mammalian cell is an Expi293F cell, a CHO cell, a 293T cell, or a NSO cell. In some embodiments, the mammalian cell is an Expi293F cell. In some embodiments, expression by a prokaryotic promoter occurs in a bacterial cell. In some embodiments, the bacterial cell is an *E. coli* cell. In some embodiments, the PES1$_1$ encodes all or a portion of an antibody. In some embodiments, the PES1$_1$ encodes a polypeptide comprising a VH domain. In some embodiments, the polypeptide further comprises a CH1 domain. In some embodiments, the PES2 encodes all or a portion of an antibody. In some embodiments, the PES2 encodes a polypeptide comprising a CH2 domain and a CH3 domain. In some embodiments, the PES1$_2$ encodes all or a portion of an antibody. In some embodiments, the PES1$_2$ encodes a polypeptide comprising a VL domain and a CL domain.

In another aspect, the invention features a nucleic acid molecule comprising a first expression cassette comprising the following components: (a) a first eukaryotic promoter (P1$_{Euk1}$); (b) a first excisable prokaryotic promoter module (ePPM$_1$) comprising the following components: (i) a 5' splice site (5'ss1$_2$); (ii) a prokaryotic promoter (P1$_{Prok1}$); and (iii) a 3' splice site (3'ss1$_1$), wherein the components of the ePPM$_1$ are operably linked to each other in a 5'-to-3' direction as 5'ss1$_2$-P1$_{Prok1}$-3'ss1$_1$; (c) a first polypeptide-encoding sequence (PES1$_1$); (d) a first 5' splice site (5'ss1$_1$); and (e) a utility peptide-encoding sequence (UPES), wherein the components of the first expression cassette are operably linked to each other in a 5'-to-3' direction as P1$_{Euk1}$-ePPM$_1$-PES1$_1$-5'ss1$_1$-UPES. In some embodiments, the first expression cassette further comprises a first nucleic acid sequence encoding a eukaryotic signal sequence (ESS1$_1$), wherein the ESS1$_1$ is positioned between the P1$_{Euk1}$ and the ePPM$_1$. In some embodiments, the ePPM$_1$ further comprises a first nucleic acid sequence encoding a prokaryotic signal sequence (PSS1$_1$), wherein the PSS1$_1$ is positioned between the P1$_{Prok1}$ and the 3'ss1$_1$. In some embodiments, the nucleic acid molecule further comprises a second expression cassette comprising a second eukaryotic promoter (P1$_{Euk2}$), (ii) a second polypeptide-encoding sequence (PES1$_2$), and (iii) a polyadenylation site (pA1), wherein the components are operably linked to each other in a 5'-to-3' direction as P1$_{Euk2}$-PES1$_2$-pA1. In some embodiments, the second expression cassette further comprises a second nucleic acid sequence encoding a eukaryotic signal sequence (ESS1$_2$), wherein the ESS1$_2$ is positioned between the P1$_{Prok2}$ and the 3'ss1$_2$. In some embodiments, the second expression cassette further comprises an excisable prokaryotic promoter module (ePPM$_2$) comprising the following components: (i) a 5' splice site (5'ss1$_3$), (ii) a prokaryotic promoter (P1$_{Prok2}$), (iii) a nucleic acid sequence encoding a prokaryotic signal sequence (PSS1$_2$), and (iv) a 3' splice site (3'ss1$_2$), wherein the components are operably linked to each other in a 5'-to-3' direction as 5'ss1$_3$-P1$_{Prok2}$-PSS1$_2$-3'ss1$_2$, and wherein the ePPM$_2$ is positioned between the P1$_{Euk2}$ and the PES1$_2$. In some embodiments, the UPES encodes all or a portion of a utility peptide selected from the group consisting of a tag, a label, a coat protein, and an adaptor protein. In some embodiments, the coat protein is selected from the group consisting of pI, pII, pIII, pIV, pV, pVI, pVII, pVIII, pIX and pX of bacteriophage M13, f1, or fd. In some embodiments, the coat protein is the pIII of bacteriophage M13.

In another aspect, the invention features a vector comprising any one of the preceding nucleic acid molecules. In another aspect, the invention features a vector set comprising a first vector and a second vector, wherein the first and second vectors comprise the first and second nucleic acid molecules, respectively, of any of the polypeptide expression systems disclosed herein.

In another aspect, the invention features host cells comprising the preceding nucleic acids, vectors, and/or vector sets. In some embodiments, the host cell is a prokaryotic cell. In some embodiments, the prokaryotic cell is a bacterial cell. In some embodiments, the bacterial cell is an *E. coli* cell. In other embodiments, the host cell is a eukaryotic cell. In some embodiments, the eukaryotic cell is a mammalian cell. In some embodiments, the mammalian cell is an Expi293F cell, a CHO cell, a 293T cell, or a NSO cell. In one embodiment, the mammalian cell is an Expi293F cell.

In a further aspect, the invention features a method for producing a polypeptide comprising culturing a host cell that comprises one or more of the preceding nucleic acids, vectors, and/or vector sets in a culture medium. In some embodiments, the method further comprises recovering the polypeptide from the host cell or the culture medium.

BRIEF DESCRIPTION OF THE DRAWINGS

FIG. 2, which encompasses FIGS. 2A and 2B, is a partial sequence diagram of the pDV2 vector. The 5'ss, 3'ss, and polypyrimidine tract (PPT) are bolded and underlined. The region encoding the 150-nt gene III sequence hybridizing to the transcript derived from pRK-Fc and pRK-Fc2 is italicized and underlined in FIG. 2B. Mutations from the wild-type PPT are bolded, italicized, and underlined. The AATAAA potential polyadenylation site in gene III in the pDV2 vector is shown above the sequence of the silent mutations (bolded, italicized, and underlined) introduced into variant pDV2 vectors pDV2c and pDC2d. FIGS. 2A and 2B disclose SEQ ID NOs: 2, 3, 9, 10, and 19-22, respectively, in order of appearance.

FIG. 3 is a partial sequence diagram of the pRK-Fc vector. The branch point consensus sequence (BP), polypyrimidine tract, and 3'ss are bolded or bolded and underlined and denoted in FIG. 3. The 150-bp anti-sense gene III sequence is italicized and underlined. The first in-frame ATG codon after the CMV promoter is bolded, italicized, and underlined. FIG. 3 discloses SEQ ID NOs: 23 and 24, respectively, in order of appearance.

FIG. 5, which encompasses FIGS. 5A and 5B, is a partial sequence diagram of the pDV2b vector. The 5'ss and 3'ss are denoted and the sequences are bolded. The polypyrimidine tract (PPT) and 9-nt G-run ISE are denoted, and bolded and highlighted, respectively. The region encoding the 150-nt gene III sequence hybridizing to the transcript derived from pRK-Fc and pRK-Fc2 is italicized in FIG. 5B. Mutations from the wild-type stII signal sequence and M13 gene III are bolded and italicized with wild-type nucleotide residues shown above the sequence. The potential AATAAA polyadenylation site motif is shown above the sequence. Amino acids in parentheses are encoded by both E. coli and also by codons created by splicing in mammalian cells. The BsiWI and RsrII restriction sites in the 3' end of the signal sequence used for variable region sequence cloning are shown above the sequences. FIGS. 5A and 5B disclose SEQ ID NOs: 2, 25, 9, 10, 19, 20, 26, and 27, respectively, in order of appearance.

FIG. 6 is a partial sequence diagram of the pRK-Fc2 vector. The branch point consensus sequence (BP), polypyrimidine tract, and 3'ss are bolded. The 9-nt G-run ISE is highlighted. The 150-bp anti-sense gene III sequence is italicized. The first ATG triplet and in-frame stop codon are underlined. The first in-frame ATG codon after the CMV promoter is bolded and italicized. The CMV promoter TATA box and transcriptional start site are indicated above the sequence. The glutamic acid residue in parenthesis is encoded by a codon created by trans-splicing in mammalian cells. FIG. 6 discloses SEQ ID NOs: 28 and 29, respectively, in order of appearance.

FIG. 9 is a partial sequence diagram of the pRK-Fab-Flag vector showing the region between the CMV promoter TATA box and the human IgG1 upper hinge region fused to the Flag tag sequence. The hinge and Flag tag sequences are followed by an SV40 polyadenylation signal (not shown). The 3'ss, including the polypyrimidine tracts and consensus branch point (BP), are indicated and bolded or bolded and underlined. The ISE sequence is denoted and bolded, underlined, and italicized. The antisense gene III sequence that mediates hybridization with the donor transcript is italicized and underlined. FIG. 9 discloses SEQ ID NOs: 30 and 31, respectively, in order of appearance.

DETAILED DESCRIPTION OF EMBODIMENTS OF THE INVENTION

I. Definitions

Figure 1:
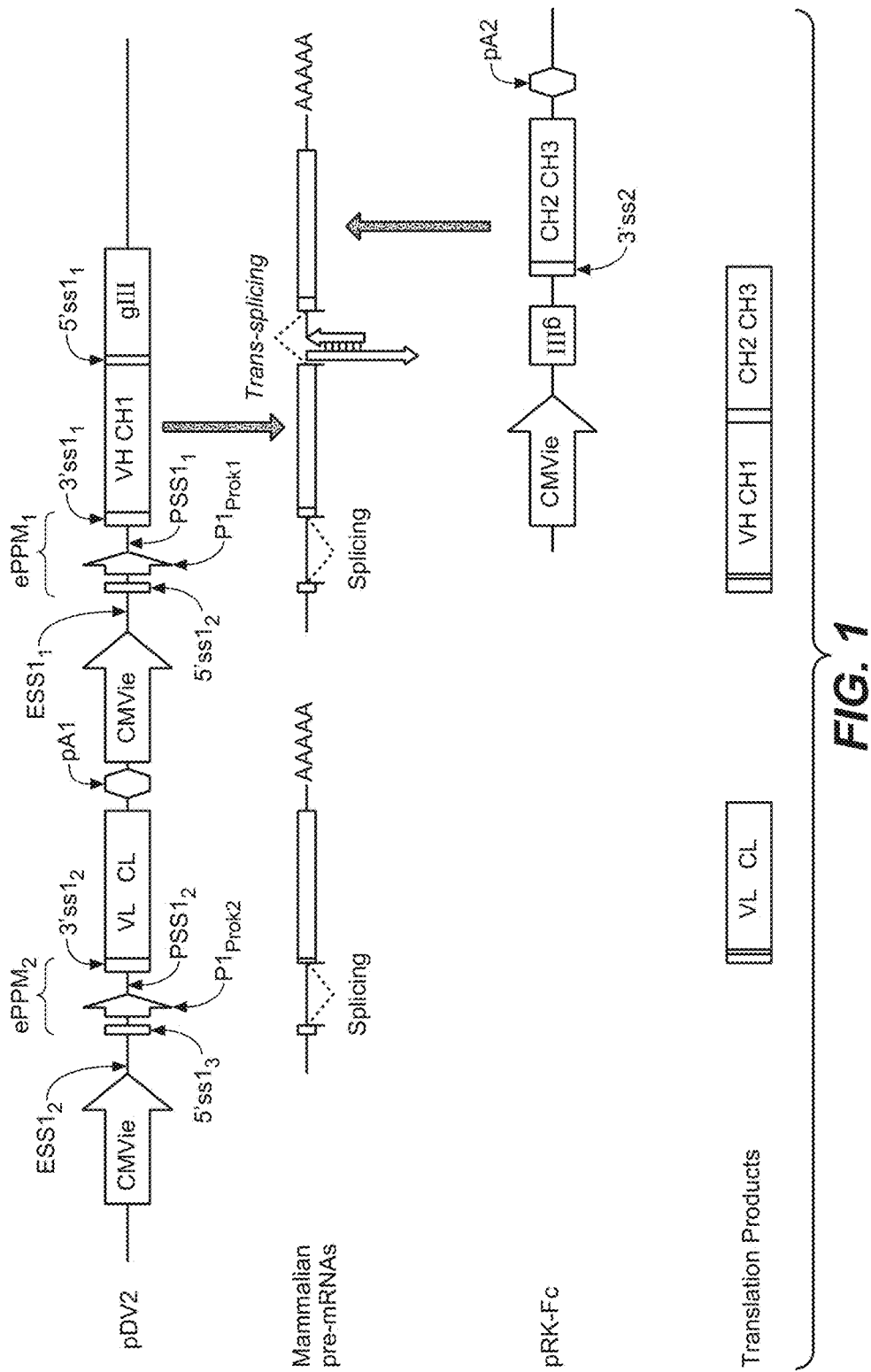
FIG. 1 is a schematic diagram showing the relative organization of the pDV2 and pRK-Fc nucleic acid molecules of a polypeptide expression system for modular protein expression. The diagram also shows the general pre-mRNA products following transcription of the nucleic acid molecules in a eukaryotic cell, the expected trans-splicing event between two generated pre-mRNA products, and the resultant products following translation of the spliced mRNA molecules.

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

The Kabat numbering system is generally used when referring to a residue in the variable domain (approximately residues 1-107 of the light chain and residues 1-113 of the heavy chain) (e.g., Kabat et al., Sequences of Immunological Interest. 5th Ed. Public Health Service, National Institutes of Health, Bethesda, Md. (1991)). The "EU numbering system" or "EU index" is generally used when referring to a residue in an immunoglobulin heavy chain constant region (e.g., the EU index reported in Kabat et al., supra). The "EU index as in Kabat" refers to the residue numbering of the human IgG1 EU antibody. Unless stated otherwise herein, references to residue numbers in the variable domain of antibodies means residue numbering by the Kabat numbering system. Unless stated otherwise herein, references to residue numbers in the heavy chain constant domain of antibodies means residue numbering by the EU numbering system.

A naturally occurring basic 4-chain antibody unit is a heterotetrameric glycoprotein composed of two identical light chains (LCs) and two identical heavy chains (HCs) (an IgM antibody consists of 5 of the basic heterotetramer units along with an additional polypeptide called J chain, and therefore contains 10 antigen binding sites, while secreted IgA antibodies can polymerize to form polyvalent assemblages comprising 2-5 of the basic 4-chain units along with J chain). In the case of IgGs, the 4-chain unit is generally about 150,000 daltons. Each LC is linked to an HC by one covalent disulfide bond, while the two HCs are linked to each other by one or more disulfide bonds depending on the HC isotype. Each HC and LC also has regularly spaced intrachain disulfide bridges. Each HC has, at the N-terminus, a variable domain (VH) followed by three constant domains (CH1, CH2, CH3) for each of the α and γ chains and four Cj domains for p and E isotypes. Each LC has, at the N-terminus, a variable domain (VL) followed by a constant domain (CL) at its other end. The VL is aligned with the VH and the CL is aligned with the first constant domain of the heavy chain (CH1). CH1 can be connected to the second constant domain of the heavy chain (CH2) by a hinge region. Particular amino acid residues are believed to form an interface between the light chain and heavy chain variable domains. The pairing of a VH and VL together forms a single antigen-binding site. For the structure and properties of the different classes of antibodies, see, e.g., Basic and Clinical Immunology, 8th edition, Daniel P. Stites, Abba I. Terr and Tristram G. Parslow (eds.), Appleton & Lange, Norwalk, Conn., 1994, page 71 and Chapter 6.

The "CH2 domain" of a human IgG Fc region usually extends from about residues 231 to about 340 of the IgG. The CH2 domain is unique in that it is not closely paired with another domain. Rather, two N-linked branched carbohydrate chains are interposed between the two CH2 domains of an intact native IgG molecule. It has been speculated that the carbohydrate may provide a substitute for the domain-domain pairing and help stabilize the CH2 domain. Burton, Molec. Immunol. 22: 161-206 (1985).

The "CH3 domain" comprises the stretch of residues C-terminal to a CH2 domain in an Fc region (i.e., from about amino acid residue 341 to about amino acid residue 447 of an IgG).

The light chain (LC) from any vertebrate species can be assigned to one of two clearly distinct types, called kappa and lambda, based on the amino acid sequences of their constant domains. Depending on the amino acid sequence of the constant domain of their heavy chains (CH), immunoglobulins can be assigned to different classes or isotypes. There are five classes of immunoglobulins: IgA, IgD, IgE, IgG, and IgM, having heavy chains designated α, δ, γ, ε, and μ, respectively. The γ and a classes are further divided into subclasses on the basis of relatively minor differences in CH sequence and function, e.g., humans express the following subclasses: IgG1, IgG2, IgG3, IgG4, IgA1, and IgA2.

The term "variable" refers to the fact that certain segments of the variable domains differ extensively in sequence among antibodies. The V domain mediates antigen binding and defines specificity of a particular antibody for its particular antigen. However, the variability is not evenly distributed across the 110-amino acid span of the variable domains. Instead, the V regions consist of relatively invariant stretches called framework regions (FRs) of 15-30 amino acids separated by shorter regions of extreme variability called "hypervariable regions" that are each 9-12 amino acids long. The variable domains of native heavy and light chains each comprise four FRs, largely adopting a beta-sheet configuration, connected by three hypervariable regions, which form loops connecting, and in some cases forming part of, the beta-sheet structure. The hypervariable regions in each chain are held together in close proximity by the FRs and, with the hypervariable regions from the other chain, contribute to the formation of the antigen-binding site of antibodies (see Kabat et al., Sequences of Proteins of Immunological Interest, 5th Ed. Public Health Service, National Institutes of Health, Bethesda, Md., 1991). The constant domains are not involved directly in binding an antibody to an antigen, but exhibit various effector functions, such as participation of the antibody in antibody dependent cellular cytotoxicity (ADCC).

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$; diabodies; linear antibodies; single-chain antibody molecules (e.g., scFv); and multispecific antibodies formed from antibody fragments.

A "Fab" fragment is an antigen-binding fragment generated by papain digestion of antibodies and consists of an entire L chain along with the variable region domain of the H chain (VH), and the first constant domain of one heavy chain (CH1). Papain digestion of antibodies produces two identical Fab fragments. Pepsin treatment of an antibody yields a single large F(ab')2 fragment which roughly corresponds to two disulfide linked Fab fragments having divalent antigen-binding activity and is still capable of cross-linking antigen. Fab' fragments differ from Fab fragments by having an additional few residues at the carboxy terminus of the CH1 domain including one or more cysteines from the antibody hinge region. Fab'-SH is the designation herein for Fab' in which the cysteine residue(s) of the constant domains bear a free thiol group. F(ab')2 antibody fragments originally were produced as pairs of Fab' fragments which have hinge cysteines between them. Other chemical couplings of antibody fragments are also known.

An "adaptor protein" as used herein refers to a protein sequence that specifically interacts with another adaptor protein sequence in solution. In one embodiment, the "adaptor protein" comprises a heteromultimerization domain. Such adaptor proteins include a leucine zipper protein or a polypeptide comprising an amino acid sequence of SEQ ID NO: 4 (cJUN(R): ASIARLEEKV KTLKAQNYEL AS TANMLREQ VAQLGGC) or SEQ ID NO: 5 (FosW(E): AS IDELQAEVEQLEERNYAL RKEVEDLQKQ AEKLGGC) or a variant thereof (amino acids in SEQ ID NO: 4 and SEQ ID NO: 5 that may be modified include, but are not limited to those that are underlined and in bold), wherein the variant has an amino acid modification wherein the modification maintains or increases the affinity of the adaptor protein to another adaptor protein, or a polypeptide comprising the amino acid sequence selected from the group consisting of SEQ ID NO: 11 (ASIARLRERVKTLRARNYELRSRAN-MLRERVAQLGGC) or SEQ ID NO: 12 (ASLDELE-AEIEQLEEENYALEKEIEDLEKELEKLGGC), or a polypeptide comprising an amino acid sequence of SEQ ID NO: 13 (GABA-R1: EEKSRLLEKE NRELEKIIAE KEERVSELRH QLQSVGGC) or SEQ ID NO: 14 (GABA-R2: TSRLEGLQSE NHRLRMKITE LDKDLEEVTM QLQDVGGC) or SEQ ID NO: 15 (Cys: AGSC) or SEQ ID NO: 16 (Hinge: CPPCPG). The nucleic acid molecule encoding for the coat protein or adaptor protein is comprised within a synthetic intron.

As used herein, "heteromultimerization domain" refers to alterations or additions to a biological molecule so as to promote heteromultimer formation and hinder homomultimer formation. Any heterodimerization domain having a strong preference for forming heterodimers over homodimers is within the scope of the invention. Illustrative examples include but are not limited to, for example, US Patent Application 20030078385 (Arathoon et al.—Genentech; describing knob into holes); WO2007147901 (Kjaergaard et al.—Novo Nordisk; describing ionic interactions); WO 2009089004 (Kannan et al.—Amgen; describing electrostatic steering effects); WO2011/034605 (Christensen et al.—Genentech; describing coiled coils). See also, for example, Pack, P. & Plueckthun, A., Biochemistry 31, 1579-1584 (1992), describing leucine zipper, or Pack et al. Bio/Technology 11, 1271-1277 (1993), describing the helix-turn-helix motif. The phrase "heteromultimerization domain" and "heterodimerization domain" are used interchangeably herein.

As used herein, the term "cloning site" refers to a nucleic acid sequence containing a restriction site for restriction endonuclease-mediated cloning by ligation of a nucleic acid sequence containing compatible cohesive or blunt ends, a region of nucleic acid sequence serving as a priming site for PCR-mediated cloning of insert DNA by homology and extension "overlap PCR stitching", or a recombination site for recombinase-mediated insertion of target nucleic acid sequences by recombination-exchange reaction, or mosaic ends for transposon mediated insertion of target nucleic acid sequences, as well as other techniques common in the art.

A "coat protein" as used herein refers to any of the five capsid proteins that are components of phage particles, including pIII, pVI, pVII, pVIII and pIX. In one embodiment, the "coat protein" may be used to display proteins or peptides (see Phage Display, A Practical Approach, Oxford University Press, edited by Clackson and Lowman, 2004, p. 1-26). In one embodiment, a coat protein may be the pIII protein or some variant, part and/or derivative thereof. For example, a C-terminal part of the M13 bacteriophage pIII coat protein (cP3), such as a sequence encoding the C-terminal residues 267-421 of protein III of M13 phage may be used. In one embodiment, the pIII sequence comprises the amino acid sequence of SEQ ID NO: 17 (AEDI-EFASGGGSGAETVESCLAKPHTENSFTNVWKDDK-TLDRYANYEGCLWNATGVVVCTGDETQ CYGTWVPIGLAIPENEGGGSEGGGSEGGGSEGGGTK-PPEYGDTPIPGYTYINPLDGTYPPGTEQNP ANPNPSLEESQPLNTFMFQNNRFRNRQGALTVYTGT-VTQGTDPVKTYYQYTPVSSKAMYDAYWNG KFRD-CAFHSGFNEDPFVCEYQGQSSDLPQP-PVNAGGGSGGGSGGGSEGGGSEGGGSEGGGSEG GGSGGGSGSGDFDYEKMANANKGAMTENADE-NALQSDAKGKLDSVATDYGAAIDGFIGDVSGLAN GNGATGDFAGSNSQMAVGDGDNSPLMNN-FRQYLPSLPQSVECRPFVFSAGKPYEFSIDCDKINLFR GVFAFLLYVATFMYVFSTFANILRNKES). In one embodiment, the pIII fragment comprises the amino acid sequence of SEQ ID NO: 18 (SGGGSGSGDFDYEK-MANANKGAMTENADENALQSDAKGKLDSVATDY-GAAIDGFIGDVSGLANGN GATGDFAGSNSQ-MAQVGDGDNSPLMNNFRQYLPSLPQSVECRPFVF-GAGKPYEFSIDCDKINLFRG VFAFLLYVATFMYVFSTFANILRNKES).

An "expression cassette" as used herein is meant a nucleic acid fragment (e.g., a DNA fragment) comprising specific nucleic acid sequences with specific biological and/or biochemical activity. The expressions "cassette", "gene cassette" or "DNA cassettes" could be used interchangeably and have the same meaning.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

The terms "linked" or "links" or "link" as used herein are meant to refer to the covalent joining of two amino acid sequences or two nucleic acid sequences together through peptide or phosphodiester bonds, respectively, such joining can include any number of additional amino acid or nucleic acid sequences between the two amino acid sequences or nucleic acid sequences that are being joined.

"Nucleic acid" or "polynucleotide," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase, or by a synthetic reaction. A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may be further modified after synthesis, such as by conjugation with a label. Other types of modifications include, for example, "caps," substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid or semi-solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl, 2'-fluoro- or 2'-azido-ribose, carbocyclic sugar analogs, alpha-anomeric sugars, epimeric sugars such as arabinose, xyloses or lyxoses, pyranose sugars, furanose sugars, sedoheptuloses, acyclic analogs and a basic nucleoside analogs such as methyl riboside. One or more phosphodiester linkages may be replaced by alternative linking groups. These alternative linking groups include, but are not limited to, embodiments wherein phosphate is replaced by P(O)S("thioate"), P(S)S ("dithioate"), "(O)NR$_2$ ("amidate"), P(O)R, P(O)OR', CO or CH$_2$ ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

A nucleic acid is "operably linked" when it is placed into a structural or functional relationship with another nucleic acid sequence. For example, one segment of DNA may be operably linked to another segment of DNA if they are positioned relative to one another on the same contiguous DNA molecule and have a structural or functional relationship, such as a promoter or enhancer that is positioned relative to a coding sequence so as to facilitate transcription of the coding sequence; a ribosome binding site that is positioned relative to a coding sequence so as to facilitate translation; or a pre-sequence or secretory leader that is positioned relative to a coding sequence so as to facilitate expression of a pre-protein (e.g., a pre-protein that participates in the secretion of the encoded polypeptide). In other examples, the operably linked nucleic acid sequences are not contiguous, but are positioned in such a way that they have a functional relationship with each other as nucleic acids or as proteins that are expressed by them. Enhancers, for example, do not have to be contiguous. Linking may be accomplished by ligation at convenient restriction sites or by using synthetic oligonucleotide adaptors or linkers.

The term "polyadenylation signal" or "polyadenylation site" is used to herein to mean a sequence sufficient to direct the addition of polyadenosine ribonucleic acid to an RNA molecule expressed in a cell.

A "promoter" is a nucleic acid sequence enabling the initiation of the transcription of a gene sequence in a messenger RNA, such transcription being initiated with the binding of an RNA polymerase on or nearby the promoter.

The term "3' splice site" is intended to mean a nucleic acid sequence, e.g. a pre-mRNA sequence, at the 3' intron/exon boundary that can be recognized and bound by splicing machinery.

The term "5' splice site" is intended to mean a nucleic acid sequence, e.g. a pre-mRNA sequence, at the 5' exon/intron boundary that can be recognized and bound by splicing machinery.

The term "cryptic splice site" is intended to mean a normally dormant 5' or 3' splice site which is activated by a mutation or otherwise and can serve as a splicing element. For example, a mutation may activate a 5' splice site which is downstream of the native or dominant 5' splice site. Use of this "cryptic" splice site results in the production of distinct mRNA splicing products that are not produced by the use of the native or dominant splice site.

The term "trans-splicing" as used herein is meant the joining of exons contained on separate, non-contiguous RNA molecules.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt et al. *Kuby Immunology*, 6$^{th}$ ed., W.H. Freeman and Co., page 91 (2007).) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., *J. Immunol.* 150:880-887 (1993); Clarkson et al., *Nature* 352:624-628 (1991).

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

II. Modular Polypeptide Expression Systems

This invention, is based, at least in part, on the discovery that pre-mRNA trans-splicing can be exploited in mammalian cells to enable modular recombinant protein expression. The concept of modular, flexible protein expression allows the precise joining of two arbitrary protein-coding sequences encoded by two different constructs into a single mRNA encoding a polypeptide chain, without any of the requirements and constraints of other protein-protein splicing methods. This concept can be adapted to simplify and extend other technologies that require mammalian cell expression of large collections of proteins with different combinations of recurring modules.

Here, we describe the generation of multiple polypeptide expression systems that enable the modular expression of different antibody formats in the context of a phage display expression system. The required nucleic acid components, vectors, host cells, and methods of using the polypeptide expression systems of the invention are described herein.

A. MODES OF CARRYING OUT THE INVENTION

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, "Molecular Cloning: A Laboratory Manual", 2$^{nd}$ edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Handbook of Experimental Immunology", 4th edition (D. M. Weir & C. C. Blackwell, eds., Blackwell Science Inc., 1987); "Gene Transfer Vectors for Mammalian Cells" (J. M. Miller & M. P. Calos, eds., 1987); "Current Protocols in Molecular Biology" (F. M. Ausubel et al., eds., 1987); "PCR: The Polymerase Chain Reaction", (Mullis et al., eds., 1994); and "Current Protocols in immunology" (J. E. Coligan et al., eds., 1991).

B. MODULAR PROTEIN EXPRESSION SYSTEM

The polypeptide expression systems of the invention can support the expression of polypeptides (e.g., fusion proteins) in the same or different (e.g., reformatted) forms. The present invention provides a means for generating such polypeptide expression systems for modular expression and production of different forms (e.g., different formats or different fusion forms) of the protein of interest in a host-cell dependent manner by using the process of trans-splicing.

1. Nucleic Acid Components of the Modular Protein Expression System a. Structure of Nucleic Acid Components of the Modular Protein Expression System The protein expression system uses at least two nucleic acid molecules that together enable the flexible, modular expression of any desired polypeptide through the process of directed pre-mRNA trans-splicing. The first nucleic acid molecule includes a first expression cassette including a eukaryotic promoter ($P1_{Euk1}$) (e.g., a cytomegalovirus (CMV) promoter, a simian virus 40 (SV40) promoter, a Moloney murine leukemia virus U3 region, a caprine arthritis-encephalitis virus U3 region, a visna virus U3 region, or a retroviral U3 region sequence), which is operably linked to a polypeptide-encoding sequence ($PES1_1$). In some instances, the polypeptide-encoding sequence encodes only a portion of the desired polypeptide, with the remaining portion being supplied by a polypeptide-encoding sequence (PES2) contained on a second nucleic acid molecule. The first nucleic acid molecule may include a 5'ss ($5'ss1_1$) (e.g., GTAAGA (SEQ ID NO: 8)) located downstream of (3' to) the $PES1_1$ but upstream of (5' to) a hybridizing sequence (HS1).

The HS1 sequence may contain a gene encoding all or a portion of a polypeptide tag, label, coat protein, and/or adaptor protein, which may be positioned in-frame with $PES1_1$ such that the expression results in the $PES1_1$-encoded protein fused to the HS1-encoded protein. In one instance, the HS1 is a gene encoding all or a portion of a coat protein selected from the group consisting of pI, pII, pIII, pIV, pV, pVI, pVII, pVIII, pIX and pX of bacteriophage M13, f1, or fd. For example, the $PES1_1$ may encode all or a portion of an antibody or Fab fragment thereof and the HS1 sequence may encode a coat protein (e.g., all or a portion of the pIII protein of bacteriophage M13, e.g., a pIII fragment comprises amino acid residues 267-421 of the pIII protein or amino acid residues 262-418 of the pIII protein), resulting in an antibody- or Fab fragment-pIII protein fusion product. In another instance, the HS1 is a gene encoding all or a portion of an adaptor protein, such as a leucine zipper, wherein the leucine zipper comprises the amino acid sequence of SEQ ID NO: 4 or 5.

In addition, the first nucleic acid molecule may encode a eukaryotic signal sequence ($ESS1_1$) located 3' to $P1_{Euk1}$ and 5' to $PES1_1$. Accordingly, the first nucleic acid molecule may include the above components linked (e.g., operably linked) to each other in a 5'-to-3' direction as $P1_{Euk1}$-$ESS1_1$-$PES1_1$-$5'ss1_1$-HS1.

The second nucleic acid molecule of the protein expression system may include a eukaryotic promoter ($P2_{Euk}$) (e.g., a cytomegalovirus (CMV) promoter or a simian virus 40 (SV40) promoter), which is operably linked to a polypeptide-encoding sequence (PES2). In some instances, the polypeptide-encoding sequence encodes only a portion of the desired polypeptide, with the remaining portion being supplied by the polypeptide-encoding sequence contained on the first nucleic acid molecule ($PES1_1$). The second nucleic acid molecule may include a 3' splice site (3'ss2) located 5' to PES2. The second nucleic acid molecule may include a hybridizing sequence capable of hybridizing to HS1 (HS2), which is located between $P2_{Euk}$ and 3'ss2. Further, the second nucleic acid molecule may include a polyadenylation site (pA2), wherein the components of the second nucleic acid molecule are operably linked to each other in a 5'-to-3' direction as $P2_{Euk}$-HS2-3'ss2-PES2-pA2.

Trans-splicing between the first and second nucleic acid pre-mRNA products in a eukaryotic cell (e.g., a mammalian cell) would therefore be induced by the hybridization of complementary sequences (i.e., HS1 and HS2) located on the separate mRNA molecules such that the lone 5' splice site of the first molecule ($5'ss1_1$) and the lone 3' splice site of the second molecule (3'ss2) are brought into proximity for trans-splicing to occur and support the formation of a the desired trans-spliced mRNA transcript. In addition, to promote trans-splicing the first nucleic acid molecule may include an intronic splice enhancer (ISE) positioned between the $5'ss1_1$ and the HS1 (ISE1). The ISE1 may, for example, include a G-run having three or more consecutive guanine residues, such as a G-run having nine consecutive guanine residues. Further, trans-splicing between the first and second nucleic acid pre-mRNA products may be induced upon their transcription in eukaryotic cells (e.g., mammalian cells, e.g., Expi293F, 293T, or CHO cells) by engineering the first nucleic acid molecule to lack a standard polyadenylation site downstream of its $PES1_1$ and/or HS1 component. This would minimize the formation of mature mRNA transcripts that would be exported to the cytoplasm before trans-splicing with the mRNA transcript of the second nucleic molecule can occur.

In some instances, it may be desirable to concomitantly express a separate polypeptide product. For example, it may be desirable to express a second polypeptide product that may self-assemble with the first polypeptide product encoded by both the first and second nucleic acid molecules to form a desired hetero-multimeric protein product (e.g., an antibody that is composed of both heavy and light chains). To this end, the first and/or second nucleic acid molecule may additionally include a second expression cassette. For example, in instances where the first nucleic acid molecule includes a second expression cassette, the second expression cassette may include a second eukaryotic promoter ($P1_{Euk2}$), (ii) a second nucleic acid sequence encoding a eukaryotic signal sequence ($ESS1_2$), (iii) a second polypeptide-encoding sequence ($PES1_2$), and (iv) a polyadenylation site (pA1), wherein the components are operably linked to each other in a 5'-to-3' direction as $P1_{Euk2}$-$ESS1_2$-$PES1_2$-pA1. In some instances, the second expression cassette may not include an $ESS1_2$ component (e.g., when secretion of the expressed polypeptide is not needed or desirable). Accordingly, the first nucleic molecule would encode two polypeptide products under to separate promoters, whereby one of the mRNA transcripts encoding one of polypeptide products of the first nucleic acid molecule was formed via directed trans-splicing with a mRNA transcript encoded by the second nucleic acid molecule. In some instances, the second expression cassette is positioned 5' to the first expression cassette. In other instances, the second expression cassette is positioned 3' to the first expression cassette.

b. Polypeptide Expression in Both Prokaryotic and Eukaryotic Cells

In some instances, the polypeptide expression system can be engineered for polypeptide expression in the context of both prokaryotic and eukaryotic cells. Accordingly, the first nucleic acid molecule may include an excisable prokaryotic promoter module (ePPM$_1$) that is positioned between the P1$_{Euk1}$ and the PES1$_1$, if expression of the polypeptide product encoded by PES1$_1$, or, in some instances, PES1$_1$ and HS1 is desired. The ePPM$_1$ may include a 5' splice site (5'ss1$_2$), a prokaryotic promoter (P1$_{Prok1}$), a nucleic acid sequence encoding a prokaryotic signal sequence (PSS1), and a 3' splice site (3'ss1$_1$) located relative to each other in a 5'-to-3' direction as 5'ss1$_2$-P1$_{Prok1}$-PSS1$_1$-3'ss1$_1$, and operably linked to drive transcription of the polypeptide encoded by PES1$_1$, or PES1$_1$ and HS1. In some instances, the ePPM$_1$ may not include a PSS1$_1$ component (e.g., when secretion of the expressed polypeptide is not needed or desirable). Thus, the ePPM$_1$ would drive the transcription of the PES1$_1$-encoded polypeptide of the first nucleic acid molecule in a prokaryotic cell. On the other hand, in a eukaryotic cell (e.g., mammalian cell), the P1$_{Euk1}$ would drive expression of the transcription of the PES1$_1$-encoded polypeptide of the first nucleic acid molecule, and the ePPM$_1$ would be removed from the pre-mRNA transcript by cis-splicing by virtue of hits flanking 5'ss1$_2$ and 3'ss1$_1$ components.

In some instances, the ePPM$_1$ also includes a polypyrimidine tract positioned between the PSS1$_1$ and the 3'ss1$_1$ (PPT1$_1$). The PPT1$_1$ may include the sequence of, for example, TTCCTTTTTTTTCTCTTTCC (SEQ ID NO: 1). The second nucleic acid molecule may also include a polypyrimidine tract (PPT2), which may, for example, be positioned between the HS2 and the 3'ss2. The PPT2 may include the sequence of, for example, TTCCTCTTTCCCTTTCTCTCC (SEQ ID NO: 7). In addition, the second nucleic acid molecule may further include an ISE positioned between the HS2 and the 3'ss2 (ISE2). The ISE2 may, for example, include a G-run having three or more consecutive guanine residues, such as a G-run having nine consecutive guanine residues.

In some embodiments in which the first nucleic acid molecule of the polypeptide expression system includes a second expression cassette, the second expression cassette may further include an excisable prokaryotic promoter module (ePPM$_2$) positioned between P1$_{Euk2}$ and PES1$_2$ and including the following components: (i) a 5' splice site (5'ss1$_3$), (ii) a prokaryotic promoter (P1$_{Prok2}$), (iii) a nucleic acid sequence encoding a prokaryotic signal sequence (PSS1$_2$), and (iv) a 3' splice site (3'ss1$_2$), whereby the components are located relative to each other in a 5'-to-3' direction as 5'ss1$_3$-P1$_{Prok2}$, PSS1$_2$-3'ss1$_2$, and operably linked to drive transcription of the polypeptide encoded by PES1$_2$. In some instances, the ePPM$_2$ may not include a PSS1$_2$ component (e.g., when secretion of the expressed polypeptide is not needed or desirable). The second excisable prokaryotic promoter module would function in a manner similar to that of the first excisable prokaryotic promoter module described above.

The prokaryotic promoter(s) of the excisable prokaryotic promoter module(s) may be a phoA, Tac, Lac, or Tphac promoter (see, e.g., Kim et al. *PLoS One.* 7(4): e35844), or another prokaryotic promoter known in the art.

An additional challenge in constructing a vector capable of expressing proteins of interest in both prokaryotic cells (e.g., *E. coli* cells) and eukaryotic cells (mammalian cells, e.g., Expi293F cells) cells arises from differences in signal sequences found in these cell types. While certain features of signal sequences are generally conserved in both prokaryotic and eukaryotic cells (e.g., a patch of hydrophobic residues located in the middle of the sequence, and polar/charged residues adjacent to the cleavage site at the N-terminus of the mature polypeptide), others are more characteristic of one cell type than the other. Moreover, it is known in the art that different signal sequences can have significant impact on expression levels in mammalian cells, even if the sequences are all of mammalian origin (Hall et al., *J of Biological Chemistry,* 265: 19996-19999 (1990); Humphreys et al., *Protein Expression and Purification,* 20: 252-264 (2000)). For instance, bacterial signal sequences typically have positively-charged residues (most commonly lysine) directly following the initiating methionine, whereas these are not always present in mammalian signal sequences.

Any signal sequence (including consensus signal sequences) which targets the polypeptide of interest to the periplasm in prokaryotes and to the endoplasmic reticulum in eukaryotes may be used, if secretion of the expressed protein is needed or desired. For example, the eukaryotic signal sequence (e.g., ESS1$_1$ or ESS1$_2$) may be derived from or include all or a portion of the murine binding immunoglobulin protein (mBiP) signal sequence (UniProtKB: accession P20029) or an antibody heavy or light chain signal sequence (e.g., a murine VH gene signal sequence). In some embodiments, the prokaryotic signal sequence (e.g., PSS1$_1$ or PSS1$_2$) may be derived from or include all or a portion of the heat-stable enterotoxin II (stII) gene. Other signal sequences that may be utilized include signal sequences from human growth hormone (hGH) (UniProtKB: accession BIA4G6), Gaussia princeps luciferase (UniProtKB: accession Q9BLZ2), and yeast endo-1,3-glucanase (yBGL2) (UniProtKB: accession P15703). The signal sequence may be a natural or synthetic signal sequence. In some embodiments, the synthetic signal sequence is an optimized signal secretion sequence that drives levels of display at an optimized level compared to its non-optimized natural signal sequence.

2. Vectors, Host Cells, and Methods of Production

The invention features vectors or vector sets including one or more of the nucleic acid molecules described above. Accordingly, the invention also features a vector set including a first vector and a second vector, wherein the first and second vectors include the first and second nucleic acid molecules, respectively, of a polypeptide expression system described above.

In addition to the components of the nucleic acid molecules described in detail above, the vectors or vector sets may include a bacterial origin of replication, a mammalian origin of replication, and/or nucleic acid which encodes for polypeptides useful as a control (e.g., gD protein) or useful for activities (e.g., protein purification, protein tagging, or protein labeling).

Methods for producing a polypeptide comprising culturing a host cell that comprises one or more of the vector(s) or vector set(s) above in a culture medium, and optionally recovering the antibody from the host cell (or host cell culture medium), are also provided.

C. PHAGE DISPLAY VECTOR SYSTEM FOR MODULAR ANTIBODY EXPRESSION AND REFORMATTING

In some embodiments, antibodies (e.g., full-length antibodies, e.g., full-length IgG antibodies, or fragments thereof, e.g., Fab fragments) can be produced using a polypeptide expression system of the invention. We demonstrate the application of modular protein expression systems by designing a phage display vector system that allows expression of different antibody formats in human cells from the same clone. The heavy chain antigen-binding region and part of the constant region encoded by the phage display vector were directly and precisely fused to sequences encoded in a second complementing construct, by joining the sequences coding different parts of the polypeptide by pre-mRNA trans-splicing during expression in cells.

Use of the polypeptide expression system for the purpose of allowing direct expression of IgG in mammalian cells without the need for subcloning of the phage Fab sequences is described in Examples 1 and 2 below. In some instances, the first nucleic acid molecule of the polypeptide expression system may designed to encode the entirety of the Fab fragment components. Accordingly, the first nucleic acid molecule may include a $PES1_1$ component that encodes a polypeptide having a VH domain and a CH1 domain of the Fab. The first nucleic acid molecule may also include a $PES1_2$ component that encodes a VL domain and a CL domain. Transcription of the first nucleic acid molecule would result in two non-contiguous pre-mRNA products, which together form a Fab fragment that may be appropriately tagged (e.g., fused to pIII of M13) for phage display purposes.

The process of reformatting the Fab fragment into a full-length IgG antibody can subsequently be accomplished by expression of the first nucleic acid molecule in a eukaryotic cell (e.g., a mammalian cell, e.g., an Expi293F cell), along with a second nucleic acid molecule that provides the remaining portion of the antibody (i.e., the CH2 and CH3 domains). For example, the second nucleic acid molecule may include a PES2 component that encodes a polypeptide having a CH2 domain and a CH3 domain. Transcription of the first and second molecules in the eukaryotic cell would result in the generation of three pre-mRNA transcripts, with the heavy chain encoding pre-mRNA transcripts being induced to undergo trans-splicing with each other to generate the reformatted full-length heavy chain of the desired IgG antibody. The processed mRNAs would then be translated and result in the production of both light chain and heavy chains of the IgG molecule, and such generation would not require the need of labor-intensive subcloning.

The ability to express different antibody formats from the same clone is useful in antibody discovery when different antibody formats such as wild-type IgG, Fab fragments, or IgG with Fc modifications for bispecific formats are required for different screening assays. The polypeptide expression system of the invention allows, in principle, any of these or additional formats by simply cloning a suitable sequence to be added after the CH1 region in the complementing plasmid. Furthermore, the modular organization of the system allows expression of new antibody formats without the need to re-create stocks of phage display libraries, as this only requires construction of a novel complementing plasmid. The nucleic acids could also be adapted to allow use of any CH1 region by shifting the 5'ss from downstream the CH1-encoding region to the J-region (FR4) in VH or in J-CH1 junction, thus separating VH and the entire constant region of the heavy chain in two different nucleic acids. The nucleic acid molecules are compatible with traditional methods for expression of Fab fragments in E. coli, by simply adding a stop codon after the sequence encoding the upper hinge. However, amber stop codons at the junction of the heavy chain and gene III sequences in Fab phage display libraries usually result in significant lower levels of display, thus requiring reformatting of clones after selection at least in the case of naïve repertoire libraries (Lee et al. *Journal of immunological methods*. 284: 119-132, 2004). Expression of Fab fragments in mammalian cells using the same methods used for IgG expression bypasses this need for reformatting, with yields comparable to those usually obtained in E. coli.

The antibodies produced by this polypeptide expression system can include recombinantly generated chimeric, humanized, and/or human antibodies. In some instances, the antibodies are antibody fragments, e.g., Fab, Fv, Fab', scFv, diabody, or F(ab')$_2$ fragments. In other instances, the antibodies are full-length antibodies, e.g., intact IgG1, IgG2, IgG3 or IgG4 antibodies or other antibodies of another class or isotype, as defined herein.

The expressed antibodies may incorporate any of the features, singly or in combination, as described in Sections 1-7 below:

1. Antibody Affinity

The antibody (e.g., Fab or full-length IgG antibody) produced by a polypeptide expression system described herein may have a dissociation constant (Kd) of $\leq 1$ μM, $\leq 100$ nM, $\leq 10$ nM, $\leq 1$ nM, $\leq 0.1$ nM, $\leq 0.01$ nM, or $\leq 0.001$ nM (e.g. $10^{-8}$ M or less, e.g. from $10^{-8}$ M to $10^{-13}$ M, e.g., from $10^{-9}$ M to $10^{-13}$ M).

In one embodiment, Kd is measured by a radiolabeled antigen binding assay (RIA) performed with the Fab version of an antibody of interest and its antigen as described by the following assay. Solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen et al., *J. Mol. Biol.* 293:865-881(1999)). To establish conditions for the assay, MICROTITER® multi-well plates (Thermo Scientific) are coated overnight with 5 μg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620), 100 pM or 26 pM [$^{125}$I]-antigen are mixed with serial dilutions of a Fab of interest (e.g., consistent with assessment of the anti-VEGF antibody, Fab-12, in Presta et al., *Cancer Res.* 57:4593-4599 (1997)). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% polysorbate 20 (TWEEN-20®) in PBS. When the plates have dried, 150 μl/well of scintillant (MICROSCINT-20™; Packard) is added, and the plates are counted on a TOP-COUNT™ gamma counter (Packard) for ten minutes. Concentrations of each Fab that give less than or equal to 20% of maximal binding are chosen for use in competitive binding assays.

According to another embodiment, Kd is measured using surface plasmon resonance assays using a BIACORE®-2000 or a BIACORE®-3000 (BIAcore, Inc., Piscataway, N.J.) at 25° C. with immobilized antigen CM5 chips at ~10 response units (RU). Briefly, carboxymethylated dextran biosensor chips (CM5, BIACORE, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 µg/ml (~0.2 µM) before injection at a flow rate of 5 µl/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN-20™) surfactant (PBST) at 25° C. at a flow rate of approximately 25 µl/min. Association rates ($k_{on}$) and dissociation rates ($k_{off}$) are calculated using a simple one-to-one Langmuir binding model (BIACORE® Evaluation Software version 3.2) by simultaneously fitting the association and dissociation sensorgrams. The equilibrium dissociation constant (Kd) is calculated as the ratio $k_{off}/k_{on}$. See, e.g., Chen et al., *J. Mol. Biol.* 293:865-881 (1999). If the on-rate exceeds $10^6 M^{-1} s^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophotometer (Aviv Instruments) or a 8000-series SLM-AMINCO™ spectrophotometer (ThermoSpectronic) with a stirred cuvette.

2. Antibody Fragments

In certain embodiments, the antibody produced by a polypeptide expression system described herein is an antibody fragment. Antibody fragments include, but are not limited to, Fab, Fab', Fab'-SH, F(ab')$_2$, Fv, and scFv fragments, and other fragments described below. For a review of certain antibody fragments, see Hudson et al. *Nat. Med.* 9:129-134 (2003). For a review of scFv fragments, see, e.g., Pluckthün, in *The Pharmacology of Monoclonal Antibodies*, vol. 113, Rosenburg and Moore eds., (Springer-Verlag, New York), pp. 269-315 (1994); see also WO 93/16185; and U.S. Pat. Nos. 5,571,894 and 5,587,458. For discussion of Fab and F(ab')$_2$ fragments comprising salvage receptor binding epitope residues and having increased in vivo half-life, see, e.g., U.S. Pat. No. 5,869,046.

Diabodies are antibody fragments with two antigen-binding sites that may be bivalent or bispecific. See, for example, EP 404,097; WO 1993/01161; Hudson et al., *Nat. Med.* 9:129-134 (2003); and Hollinger et al., *Proc. Natl. Acad. Sci. USA* 90: 6444-6448 (1993). Triabodies and tetrabodies are also described in Hudson et al., *Nat. Med.* 9:129-134 (2003).

Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, Mass.; see, e.g., U.S. Pat. No. 6,248,516 B1).

3. Chimeric and Humanized Antibodies

In certain embodiments, the antibody (e.g., Fab or full-length IgG antibody) produced by a polypeptide expression system described herein is a chimeric antibody. Certain chimeric antibodies are described, e.g., in U.S. Pat. No. 4,816,567; and Morrison et al., *Proc. Natl. Acad. Sci. USA*, 81:6851-6855 (1984)). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro and Fransson, *Front. Biosci.* 13:1619-1633 (2008), and are further described, e.g., in Riechmann et al., *Nature* 332:323-329 (1988); Queen et al., *Proc. Nat'l Acad. Sci. USA* 86:10029-10033 (1989); U.S. Pat. Nos. 5,821,337, 7,527,791, 6,982,321, and 7,087,409; Kashmiri et al., *Methods* 36:25-34 (2005) (describing SDR (a-CDR) grafting); Padlan, *Mol. Immunol.* 28:489-498 (1991) (describing "resurfacing"); Dall'Acqua et al., *Methods* 36:43-60 (2005) (describing "FR shuffling"); and Osbourn et al., *Methods* 36:61-68 (2005) and Klimka et al., *Br. J. Cancer,* 83:252-260 (2000) (describing the "guided selection" approach to FR shuffling).

Human framework regions that may be used for humanization include but are not limited to: framework regions selected using the "best-fit" method (see, e.g., Sims et al. *J. Immunol.* 151:2296 (1993)); framework regions derived from the consensus sequence of human antibodies of a particular subgroup of light or heavy chain variable regions (see, e.g., Carter et al. *Proc. Natl. Acad. Sci. USA*, 89:4285 (1992); and Presta et al. *J. Immunol.*, 151:2623 (1993)); human mature (somatically mutated) framework regions or human germline framework regions (see, e.g., Almagro and Fransson, *Front. Biosci.* 13:1619-1633 (2008)); and framework regions derived from screening FR libraries (see, e.g., Baca et al., *J. Biol. Chem.* 272:10678-10684 (1997) and Rosok et al., *J. Biol. Chem.* 271:22611-22618 (1996)).

4. Human Antibodies

In certain embodiments, the antibody (e.g., Fab or full-length IgG antibody) produced by a polypeptide expression system described herein is a human antibody. The human antibody may be a recombinant human antibody that was originally prepared, and whose sequence was then identified, using various techniques known in the art. Human antibodies are described generally in van Dijk and van de Winkel, *Curr. Opin. Pharmacol.* 5: 368-74 (2001) and Lonberg, *Curr. Opin. Immunol.* 20:450-459 (2008).

5. Library-Derived Antibodies

By virtue of the utility of the polypeptide expression system described herein being useful in phage display systems, antibodies (e.g., Fab or full-length IgG antibodies) produced by a polypeptide expression system of the invention may have been isolated by screening combinatorial libraries for antibodies with the desired activity or activities.

See, for example, Hoogenboom et al. in *Methods in Molecular Biology* 178:1-37 (O'Brien et al., ed., Human Press, Totowa, N.J., 2001) and also, e.g., in the McCafferty et al., *Nature* 348:552-554; Clackson et al., *Nature* 352: 624-628 (1991); Marks et al., *J. Mol. Biol.* 222: 581-597 (1992); Marks and Bradbury, in *Methods in Molecular Biology* 248:161-175 (Lo, ed., Human Press, Totowa, N.J., 2003); Sidhu et al., *J. Mol. Biol.* 338(2): 299-310 (2004); Lee et al., *J. Mol. Biol.* 340(5): 1073-1093 (2004); Fellouse, *Proc. Natl. Acad. Sci. USA* 101(34): 12467-12472 (2004); and Lee et al., *J. Immunol. Methods* 284(1-2): 119-132(2004).

6. Multispecific Antibodies

In certain embodiments, the antibody (e.g., Fab or full-length IgG antibody) produced by a polypeptide expression system described herein is a multispecific antibody, e.g., a bispecific antibody. Multispecific antibodies are monoclonal antibodies that have binding specificities for at least two different sites. In certain embodiments, one of the binding specificities is for a first antigen and the other is for any other antigen. In certain embodiments, bispecific antibodies may bind to two different epitopes of the first antigen. Bispecific antibodies may also be used to localize cytotoxic agents to cells which express the first antigen. Bispecific antibodies can be prepared as full length antibodies or antibody fragments.

Engineered antibodies with three or more functional antigen binding sites, including "Octopus antibodies," are also included herein (see, e.g. US 2006/0025576A1).

The antibody or fragment herein also includes a "Dual Acting FAb" or "DAF" comprising an antigen binding site that binds to a first antigen as well as another, different antigen (see, US 2008/0069820, for example).

7. Antibody Variants

In certain embodiments, amino acid sequence variants of the antibodies provided herein are contemplated. For example, it may be desirable to improve the binding affinity and/or other biological properties of the antibody. Amino acid sequence variants of an antibody may be prepared by introducing appropriate modifications into one or more of the nucleic acid molecules encoding all or a portion of the antibody. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

In certain embodiments, a collection of antibody variants having one or more amino acid substitutions relative to one another can be produced by the expression systems and methods of the invention. Sites of interest for substitutional mutagenesis include the HVRs and FRs. Conservative substitutions are shown in Table 1 under the heading of "conservative substitutions." More substantial changes are provided in Table 1 under the heading of "exemplary substitutions," and as further described below in reference to amino acid side chain classes. Amino acid substitutions may be introduced into an antibody of interest and the products screened for a desired activity, e.g., retained/improved antigen binding, decreased immunogenicity, or improved ADCC or CDC.

TABLE 1

Exemplary and Preferred Amino Acid Substitutions

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:
(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

One type of substitutional variant involves substituting one or more hypervariable region residues of a parent antibody (e.g., a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g. binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, *Methods Mol. Biol.* 207:179-196 (2008)), and/or SDRs (a-CDRs), with the resulting variant VH or VL being tested for binding affinity. Affinity maturation by constructing and reselecting from secondary libraries has been described, e.g., in Hoogenboom et al. in *Methods in Molecular Biology* 178:1-37 (O'Brien et al., ed., Human Press, Totowa, N.J., (2001). In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may be outside of HVR "hotspots" or SDRs. In certain embodiments of the variant VH and VL sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham and Wells (1989) *Science*, 244:1081-1085. In this method, a residue or group of target residues (e.g., charged residues such as arg, asp, his, lys, and glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g. for ADEPT) or a polypeptide which increases the serum half-life of the antibody.

Although we describe the concept of modular protein expression through pre-mRNA trans-splicing in the context of a phage antibody display vector system in detail herein, the application of the concept, as exemplified by use of the nucleic acid molecules, vectors, vector sets, host cells, and methods described herein, can be adapted and extended, for example, to other technologies that require mammalian cell expression of large collections of proteins with different combinations of recurring modules.

III. Examples

The following are examples of the invention. It is understood that various other embodiments may be practiced, given the general description provided above.

Example 1. Generation of a Modular Protein Expression System for Antibody Reformatting in the Context of Phage Display Vectors We describe the generation of polypeptide expression systems for the modular expression and production of polypeptides. The invention is based, at least in part, on experimental findings that demonstrate that pre-mRNA trans-splicing can be exploited in mammalian cells to enable modular recombinant protein expression. The concept of modular protein expression allows the precise joining of two arbitrary protein-coding sequences encoded by two different constructs into a single mRNA encoding a polypeptide chain, without any of the requirements and constraints of other protein-protein splicing methods. The concept of modular protein expression through pre-mRNA trans-splicing can be adapted to simplify and extend other technologies that require mammalian cell expression of large collections of proteins with different combinations of recurring modules. For example, this concept will find application in other settings requiring expression of combinations of fusion protein partners or mutations in single polypeptides. This technology is both simple and powerful, allowing application at any scale and has broad significance for the field of recombinant protein expression in mammalian cells, the basis for much of modern biotechnology.

Here, we describe the generation of such a polypeptide expression system that enables the modular expression of different antibody formats in the context of a phage display expression system. Phage display is widely used in discovery and engineering of antibody fragments for development of therapeutic and reagent antibodies (McCafferty et al. *Nature.* 348: 552-554, 1990; Sidhu. *Current opinion in biotechnology.* 11: 610-616, 2000; Smith. *Science.* 228: 1315-1317, 1985). Phage display traditionally allows for the rapid selection of antigen-specific binders but limited screening of the selected antibody fragments. Detailed characterization of the antibody fragments often requires expression of full-length immunoglobulin G (IgG), usually expressed in mammalian cells. However, one limiting step in this process is the reformatting of the phage clones to mammalian expression vectors for IgG expression. Although high-throughput subcloning methods can be used to reformat a large number of clones, these methods are usually relatively labor intensive and yield many clones that will not be used beyond the screening stage.

To bypass the need for subcloning and enable modular protein expression, we generated a first nucleic acid molecule: dual host vector, pDV2 (FIG. 1). Unlike the previously described dual vector, pDV, which contains an IgG expression cassette with an engineered signal sequence for expression of the heavy chain in either bacterial or mammalian cells and requires co-transfection of mammalian cells with a mammalian expression vector expressing the light chain for full IgG expression (Tesar et al. *Protein engineering, design & selection: PEDS.* 26: 655-662, 2013), pDV2 contains a bacterial promoter and most of a stII signal sequence embedded in an intron that is removed by splicing in mammalian cells.

The stII signal sequence in pDV2 was modified to include both a 3' splice site (3'ss) and an optimized polypyrimidine tract (PPT) before the 3'ss. This required introducing three relatively conservative amino acid substitutions in the stII signal sequence, which did not affect display of Fab fragments on phage (FIG. 2). To allow modular, flexible expression of antibody formats from the same clone, we did not add a full intron and exon encoding constant regions downstream from the region encoding the CH1 domain. Instead, we sought to add these heavy chain sequences in trans from a second nucleic acid molecule. To achieve this we exploited the process of pre-mRNA trans-splicing, the joining of two different pre-mRNAs to form a single mature mRNA. Trans-splicing can be induced in mammalian cells by bringing pre-mRNAs with lone 5'ss and 3'ss by hybridization of complementary sequences downstream from the 5'ss and upstream from the 3'ss to form a single, non-covalently linked pre-mRNA that is then spliced as a normal pre-mRNA (Konarska et al. *Cell.* 42: 165-171, 1985; Puttaraju et al. *Nature biotechnology.* 17: 246-252, 1999; Solnick. *Cell.* 42: 157-164, 1985). In this particular polypeptide expression system, we used a 150-bp fragment of the M13 gene III (gIII) as the hybridizing sequence (FIG. 1). This gene III sequence follows a previously described optimized GTAAGA 5'ss at the 3' boundary of the sequence encoding CH1 (Tesar et al. *Protein engineering, design & selection: PEDS.* 26: 655-662, 2013).

Figure 4A:
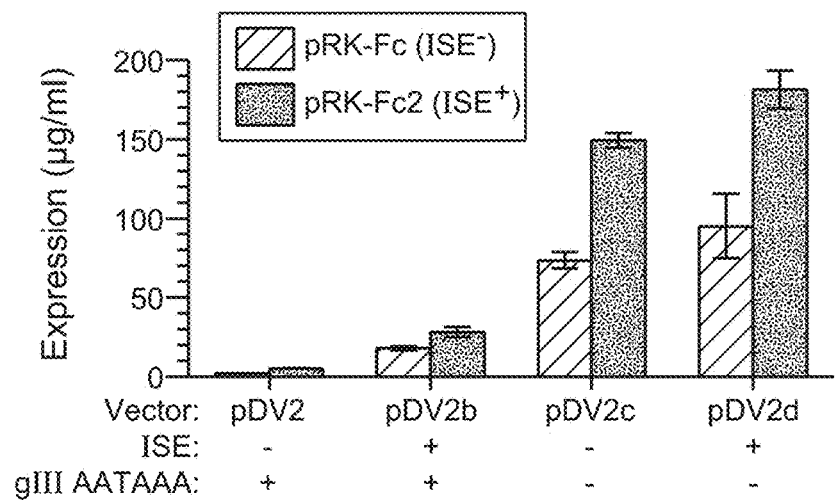
FIG. 4A is a graph showing the effect of adding ISE sequences or removing the potential polyadenylation motif in gene III in pDV2 and complementing pRK-Fc and pRK-Fc2 vectors on expression levels of IgG (in g/ml) in Expi293F cells.

To complete the polypeptide expression system, we generated a second nucleic acid molecule, pRK-Fc, which is a complementing plasmid that expresses a pre-mRNA containing a 150-nt antisense gene III sequence followed by a linker sequence, a consensus branch point, and a PPT, as well as a 3'ss followed by the hinge, CH2 and CH3 regions in one exon, and an SV40 polyadenylation signal (FIGS. 1 and 3). This transcript encodes no signal sequence, and the first two potential initiation codons are located in the antisense gene III sequence and in the hinge region, out of frame. Thus, except for the 5'ss, all the other sequences required for splicing are encoded by pRK-Fc, rather than pDV2. Co-transfection of Expi293F cells (Invitrogen) with pDV2 and pRK-Fc resulted in a baseline but detectable expression level of IgG (FIG. 4A).

Example 2. Generation of an Optimized Modular Protein Expression System for Antibody Reformatting in the Context of Phage Display Vectors The baseline IgG yields achieved by pDV2 and pRK-Fc could be due to the lack of sequences required for efficient trans-splicing or sequences in the vector that inhibit trans-splicing. Nucleotide motifs in both exons and introns can act as splicing enhancers or suppressors or both, depending on their location. For the purpose of vector design, intronic splice enhancers (ISE) can be more easily added, as these would not likely affect coding sequences in mammalian cell expression. One well-described ISE is composed of a sequence of 3 or more consecutive guanine residues, or a G-run, located close to the intron boundaries, which are bound by heterogeneous nuclear ribonucleoproteins H or F to enhance splicing (Wang et al. *Nature structural & molecular biology.* 19: 1044-1052, 2012; Xiao et al. *Nature structural & molecular biology.* 16: 1094-1100, 2009). In addition, purine-rich intron sequences close to the 5'ss not limited to G-runs have also been shown to enhance splicing (Hastings et al. *RNA.* 7: 859-874, 2001).

Thus, we created a variant of pDV2, pDV2b, that includes a 23-base pair (bp) purine-rich region 26-bp downstream from the 5'ss, which has a 9-nt G-run in the region encoding the linker between the upper hinge and C-terminal part of the M13 bacteriophage pIII coat protein (cP3) as well as a second 4-nt G-run 10 nt downstream (FIG. 5). This variant changes the Gly-Arg-Pro linker between upper hinge and cP3 to three Gly residues. The vector did not include a standard polyadenylation site for the heavy chain cassette. The reason for this was to attempt to minimize the formation of mature heavy chain mRNAs from the vector, which would then be exported to the cytoplasm before trans-splicing could occur and potentially lead to expression of Fab-cP3 fusion protein. The pRK-Fc molecule was also optimized. Intronic G-runs nearby the 3'ss have also been shown to stimulate splicing in vitro (Martinez-Contreras. *PLoS biology.* 4: e21, 2006). Therefore, a 9-nt ISE was also added upstream from the branch site to generate the optimized complementing plasmid pRK-Fc2 (FIG. 6). Co-transfection of human Expi293F cells with pDV2 and pRK-Fc (ISE−) or pRK-Fc2 (ISE+) resulted in a baseline level of IgG expression (FIG. 4A). Co-transfection of Expi293F cells with the ISE+ pDV2b plasmid and either pRK-Fc or pRK-Fc2 resulted in higher levels of IgG expression with the highest expression levels, up to 25 g/ml, yielded by co-transfecting the ISE+ plasmids pDV2b and pRK-Fc2, indicating that ISE sequences in both transcripts enhance the efficiency of trans-splicing.

The baseline IgG expression levels in transfected Expi293F cells were associated with apparent cell lysis 7 days post-transfection, also observed when pDV2 or pDV2b but not pRK-Fc or pRK-Fc2 were transfected alone. Analysis of transfected cell lysates by Western blotting with an anti-M13 p3 antibody revealed a polypeptide with an apparent molecular weight of about 41 kDa (FIG. 12, bottom panel, lanes 3 to 6), consistent with the expression of an IgG1 Fd fragment (VH-CH1-upper hinge) fused to the M13 cP3 peptide. The expression of this polypeptide was higher in cells transfected with pDV2 or pDV2b without a complementing plasmid. The results indicated that the pDV2 and pDV2b plasmids were capable of expressing a mature mRNA encoding a potentially toxic product despite the fact that both lack a mammalian polyadenylation site in the vector downstream from the heavy chain cassette.

Figure 12:
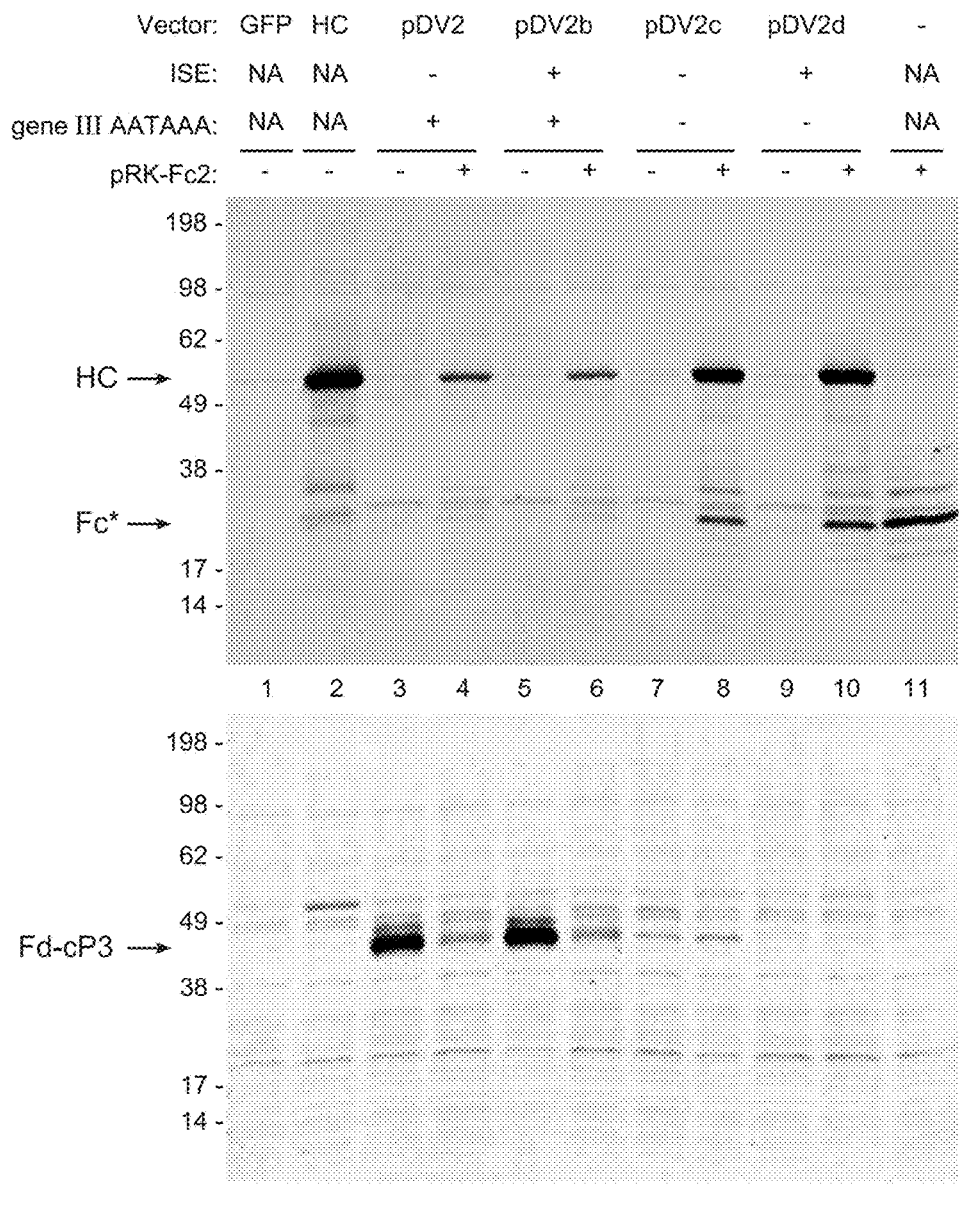
FIG. 12 is a set of Western blots showing expression of Mab1 heavy chain and Fd-cP3 fusion protein in Expi293F cells co-transfected with pDV2 variants and pRK-Fc2. Transfected Expi293F lysates were reduced with dithiothreitol (DTT) and analyzed by Western blotting with anti-IgG1 Fc (top panel) or anti-M13 $p^3$ (bottom panel) antibodies. The GFP and HC control vectors express green fluorescent protein and human IgG1 heavy chain, respectively. HC indicates the full-length human IgG1 heavy chain. Gene III AATAAA indicates the presence of the potential polyadenylation site in gene III. Fc* indicates a presumed cytoplasmic, N-terminally truncated Fc fragment expression product. NA, not applicable.

Visual inspection of the gene III sequence encoding cP3 revealed an AATAAA motif that could possibly act as a polyadenylation site (FIG. 2). We introduced two silent mutations at this site to generate plasmids pDV2c (ISE−) and pDV2d (ISE+) to test whether this would reduce toxicity and improve protein expression in mammalian cells. Co-transfection of Expi293F cells with pRK-Fc and either pDV2c or pDV2d resulted in approximately 6-fold higher levels of IgG expression relative to the pDV2 and pDV2b vectors with the potential polyadenylation site in gene III (FIG. 4A). This increase in IgG expression levels was associated with high viability of transfected cells and with significantly reduced or undetectable expression of Fd-cP3 fusion protein in transfected cells (FIG. 12, lower panel, lanes 7 to 10). This indicates that the presence of a potential polyadenylation site in the donor vector within gene III leads to unwanted protein expression from the donor plasmid alone that has a significant negative impact on protein expression. Co-transfection of Expi293F cells with pDV2c or pDV2d and the ISE+ pRK-Fc2 complementing vector resulted in an additional 2-fold increase in IgG expression compared to co-transfections with the ISE− pRK-Fc vector (FIG. 4A). These results indicate that the major factor determining baseline protein expression in the pDV2 vector was the presence of the potential polyadenylation site in gene III, whereas addition of an ISE has a minor effect on protein expression when the potential gene III polyadenylation motif is absent. In contrast, addition of an ISE in the complementing pRK-Fc2 plasmid results in an approximately 2-fold higher IgG yield when co-transfected with a pDV2 variant without a potential polyadenylation site in gene III (FIG. 4A).

Figure 4B:
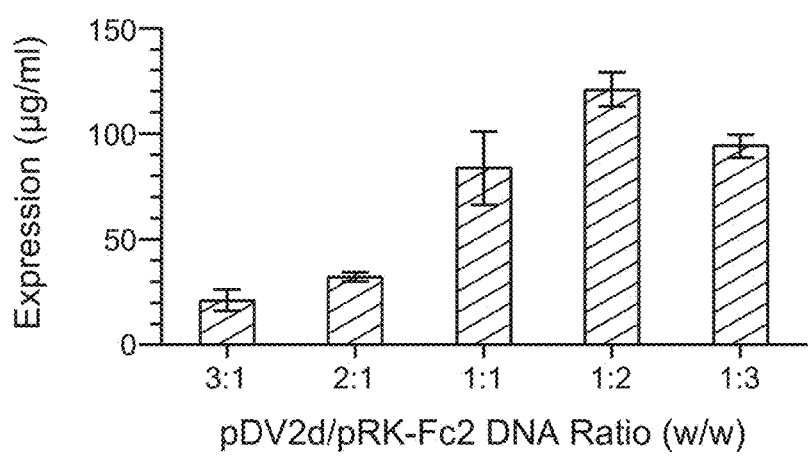
FIG. 4B is a graph showing the effect of plasmid ratios of pDV2c and pRK-Fc2 on expression levels of IgG (in g/ml) in Expi293F cells. The values shown are average and standard error of the mean of a representative experiment of two independent experiments done in triplicate.
Figures 7A, 7B:
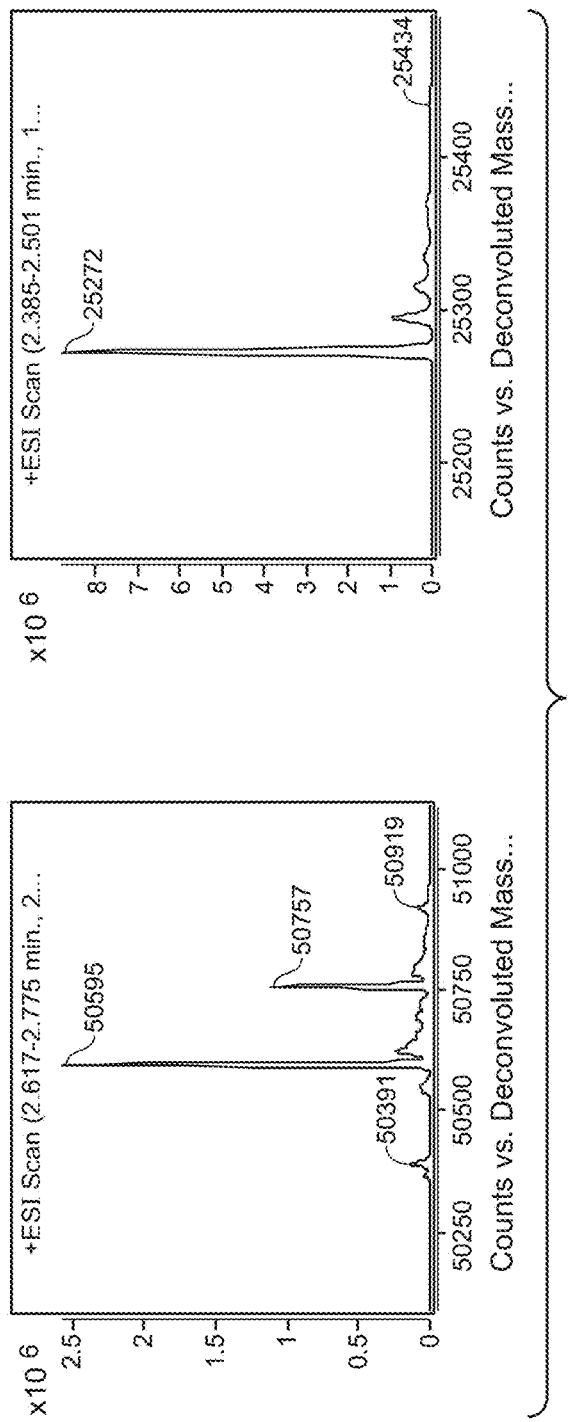
FIG. 7A is a set of graphs showing the deconvoluted mass from mass spectrometry analysis of the heavy (left panel) and light (right panel) chains of purified IgG expressed in Expi293F cells.
FIG. 7B is a table showing the expected and observed masses of for both heavy and light chains in FIG. 7A.
Figure 8A:
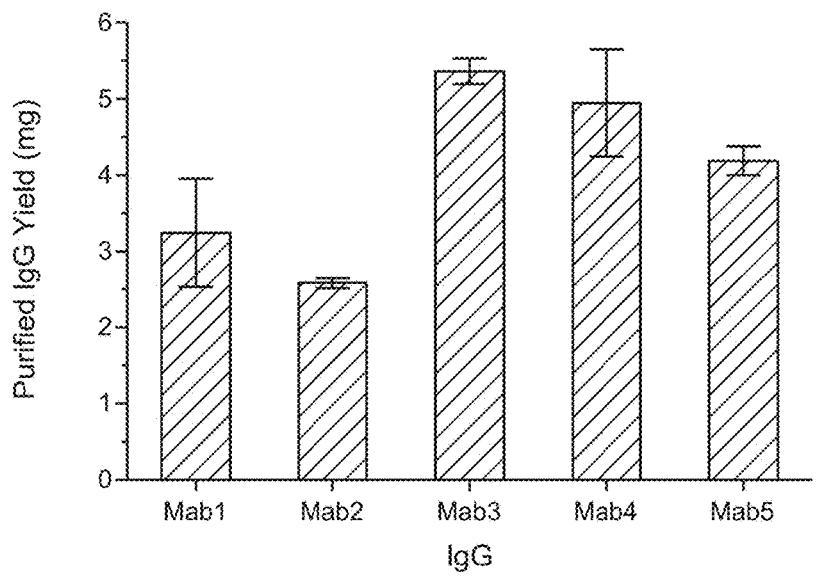
FIG. 8A is a graph showing yields (in mg) of IgG molecules of 5 different specificities purified from the supernatant (30 ml) of Expi293F cell cultures co-transfected with the pDV2d (containing ISE and without the AATAAA motif in gene III) and the pRK-Fc2 vectors. n=3. Error bars show standard error of the mean.
Figure 8B:
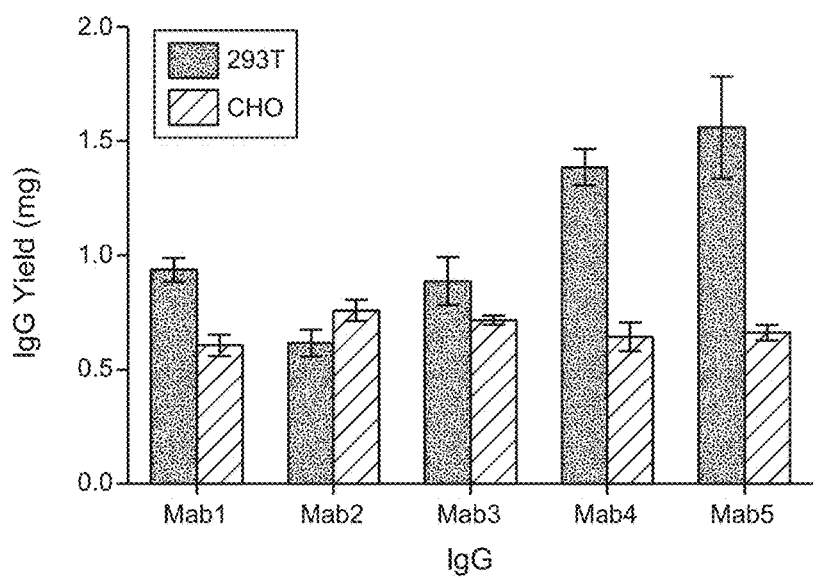
FIG. 8B is a graph showing yields (in mg) of IgG molecules of 5 different specificities purified from the supernatant (30 ml) of 293T and CHO cell cultures co-transfected with the pDV2d (containing ISE and without the AATAAA motif in gene III) and the pRK-Fc2 vectors. n=4. Error bars show standard error of the mean.
Figure 13:
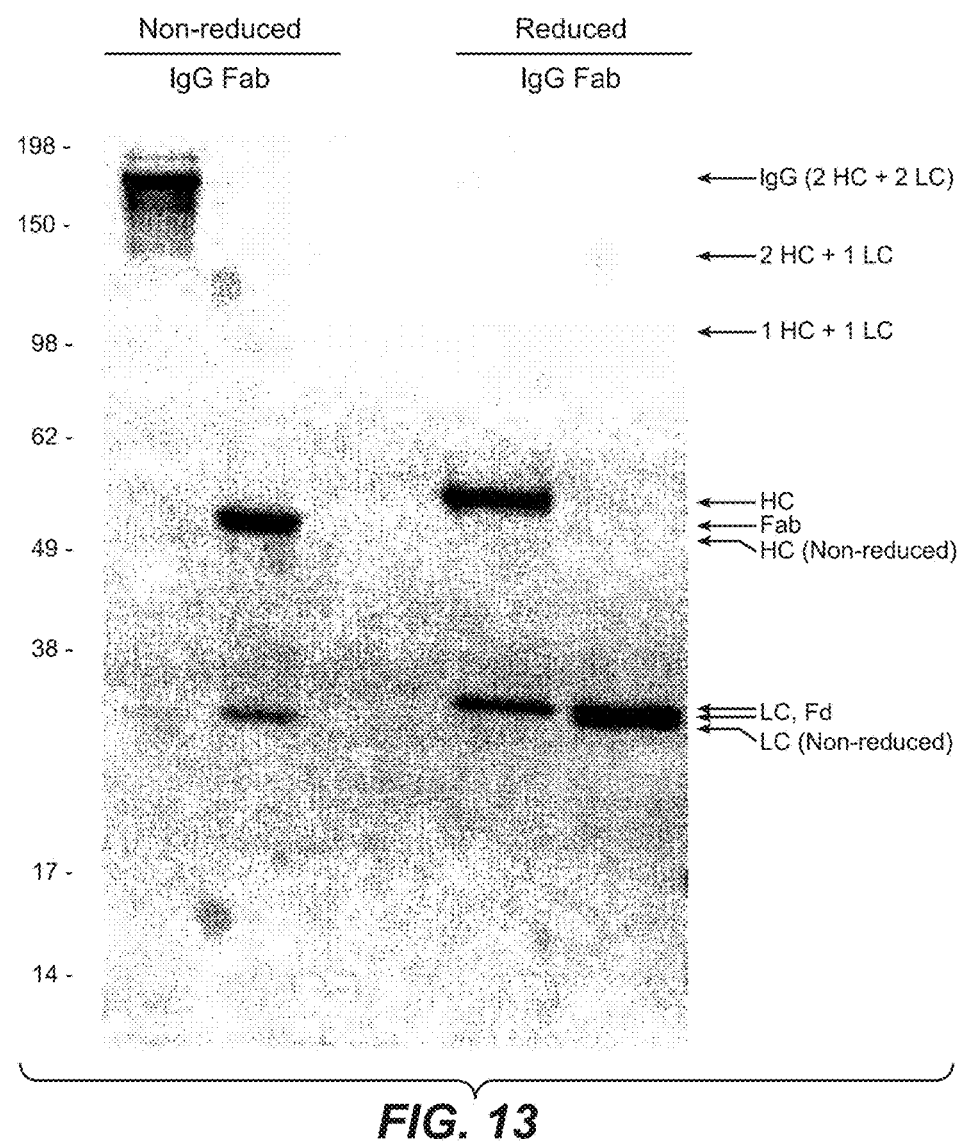
FIG. 13 is a sodium dodecyl sulfate polyacrylamide gel electrophoresis (SDS-PAGE) gel showing analysis of purified IgG and Fab fragments expressed in Expi293F cells. Purified IgG and Fab expressed from supernatants of Expi293F cells co-transfected with pDV2d and pRK-Fc2 (IgG) or pRK-Fab-F (Fab fragment) were purified, resolved by 4-20% gradient SDS-PAGE under reducing or non-reducing conditions and stained with Coomassie Brilliant Blue. The identities of the bands are shown on the right. HC, heavy chain. LC, light chain. Fd, heavy chain Fd fragment (VH+CH1+upper hinge). The HC and LC (non-reduced) bands are heavy and light chains that fail to form interchain disulfide bonds but may have intrachain disulfide bonds in IgG samples. The approximately 25-kDa band in the non-reduced Fab sample has co-migrating heavy and light chains that did not form interchain disulfide bonds but that may have intrachain disulfide bonds.

Further optimization of protein expression was achieved by determining the optimal DNA ratios for transfection. Using a 2:1 excess of the complementing plasmid pRK-Fc2 relative to pDV2d resulted in the highest IgG expression yields in this system (FIG. 4B). Using pDV2d and pRK-Fc2 with the optimized DNA ratios the yield of purified IgG from 30 ml of transfected Expi293F cell supernatants was 3.2±1.2 mg (n=3). The IgG purified from the Expi293F cells co-transfected with these plasmids was indistinguishable from the same IgG expressed by conventional expression vectors by mass spectrometry and SDS-PAGE (FIGS. 7A-7B and FIG. 13). Co-transfection of Expi293F cells with pDV2d encoding variable regions of different specificities and pRK-Fc2 with the optimized DNA ratios resulted in high IgG expression between 2.5 to 5.5 mg of IgG purified from 30 ml of transfected Expi293F cell supernatants (FIG. 8A). The polypeptide expression system is not limited to the use of Expi293F cells to achieve high expression levels. Other mammalian cell lines widely used for IgG expression, such as 293T and CHO cells, were also effective. Co-transfection of 293T or CHO cells with pDV2d expressing variable regions of different specificities and pRK-Fc2 resulted in high IgG expression (FIG. 8B).

The pRK-Fc2 vector was modified for expression of Fab fragments when co-transfected with the pDV2 plasmids. The sequences encoding the lower hinge and Fc regions in pRK-Fc2 were removed and replaced with a Flag tag to yield the pRK-Fab-Flag vector (FIG. 9). The yield of purified Fab fragments purified from 30 ml supernatants of Expi293F cells co-transfected with pDV2d and pRK-Fab-Flag was 0.8±0.06 mg (mean±standard deviation, n=3). The structural correctness of the purified Flag-tagged Fab fragment was confirmed by mass spectrometry and SDS-PAGE (FIG. 13). The observed heavy chain mass was 25,169 Da, close to the expected mass of 25,172 Da when excluding the clipped C-terminal lysine.

The expression of N-terminally truncated proteins from the complementing transcript has been observed in trans-splicing systems for gene therapy (Monjaret et al. *Molecular therapy* 22: 1176-1187, 2014). This is due to the complementing transcript encoding the 3' exon having all the elements necessary for the formation of a mature mRNA, which could lead to translation from internal initiation codons. We observed by Western blotting of lysates of cells transfected with pRK-Fc2 the expression of a polypeptide consistent with an Fc fragment translated from the first in-frame ATG codon (FIG. 12, top panel, lane 11). This polypeptide presumably lacks a secretion signal sequence and should be expressed in the cytoplasm only. Although this product could be released into the culture media by cell lysis, we did not observe it in purified IgG samples by SDS-PAGE (FIG. 13, lane 2) and mass spectrometry. The expression of this truncated product was reduced but not eliminated when pDV2c or pDV2d are co-transfected into cells (FIG. 12, top panel, lanes 8 and 10). Insertion of an out-of-frame open reading frame with an optimal translation initiation site in the intron region upstream from potential Fc initiation codons did not significantly reduce expression of the truncated Fc product.

Figure 14:
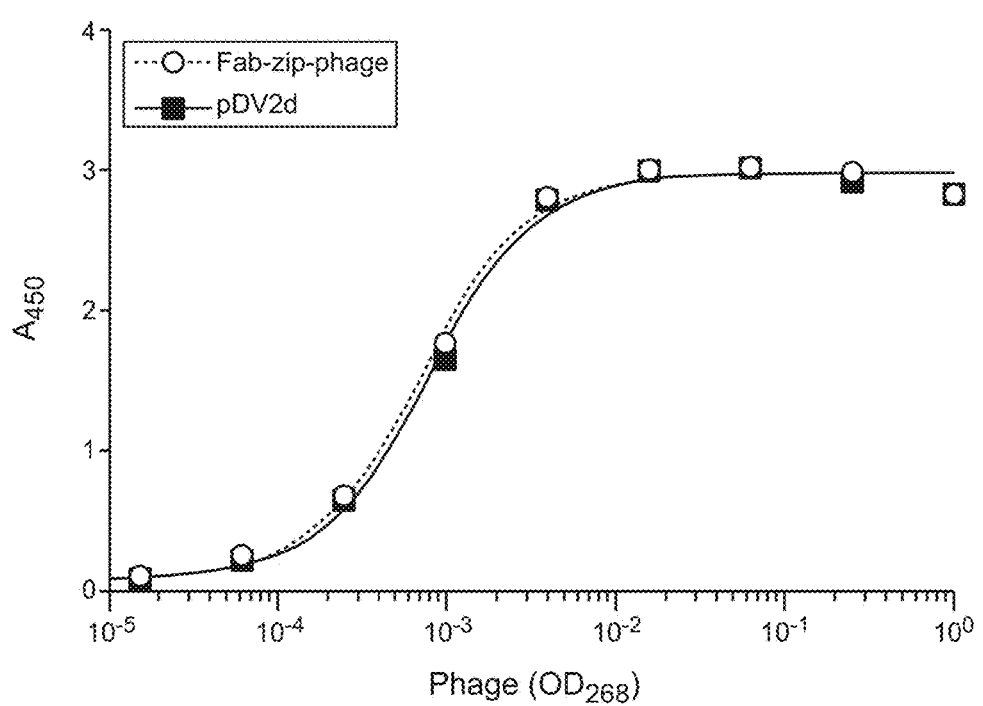
FIG. 14 is a graph showing display of Fab fragments on phage with phagemid pDV2 detected by phage enzyme-linked immunosorbant assay (ELISA). Fab-zip-phage was produced by infecting E. coli cells harboring pFab-zip phagemid with M13KO7 helper phage. The pDV2 phage was produced by infecting E. coli cells harboring pDV2d vector with Amber-2614 KO7 phage.

An important property of phage display vectors that determines selection efficiency is the level of antibody fragment display on phage particles that is achieved. Using the previously described Amber-2614 KO7 helper phage with reduced p3 expression in *E. coli* SupE suppressor strains, the levels of Fab fragment display achieved with the pDV2d vector were comparable to the Fab display levels achieved with a specialized Fab display vector, Fab-zip-phage, using the standard M13KO7 helper phage (FIG. 14).

The ability to express different antibody formats from the same clone is useful in antibody discovery when different antibody formats, such as wild-type IgG, Fab fragments, or IgG with Fc modifications for bispecific formats, are required for different screening assays. The vector set allows, in principle, any of these or additional formats by simply cloning a suitable sequence to be added after the CH1 region in the complementing plasmid. Furthermore, the modular organization of the system allows expression of new antibody formats without the need to re-create stocks of phage display libraries, as this only requires construction of a novel complementing plasmid. The dual vector could also be adapted to allow use of any CH1 region by shifting the 5'ss from downstream the CH1-encoding region to the J-region (FR4) in VH or in J-CH1 junction, thus separating the VH and the entire constant region of the heavy chain in two different plasmids. The pDV2 vectors are compatible with traditional methods for expression of Fab fragments in *E. coli*, by simply adding a stop codon after the sequence encoding the upper hinge, with the knowledge that amber stop codons at the junction of the heavy chain and gene III sequences in Fab phage display libraries usually result in significant lower levels of display, thus requiring reformatting of clones after selection at least in the case of naïve repertoire libraries (Lee et al. *Journal of immunological methods*. 284: 119-132, 2004). Expression of Fab fragments in mammalian cells using the same methods used for IgG expression bypasses this need for reformatting, with yields comparable to those usually obtained in *E. coli*.

Example 3. Modular Protein Expression Systems

Figure 10:
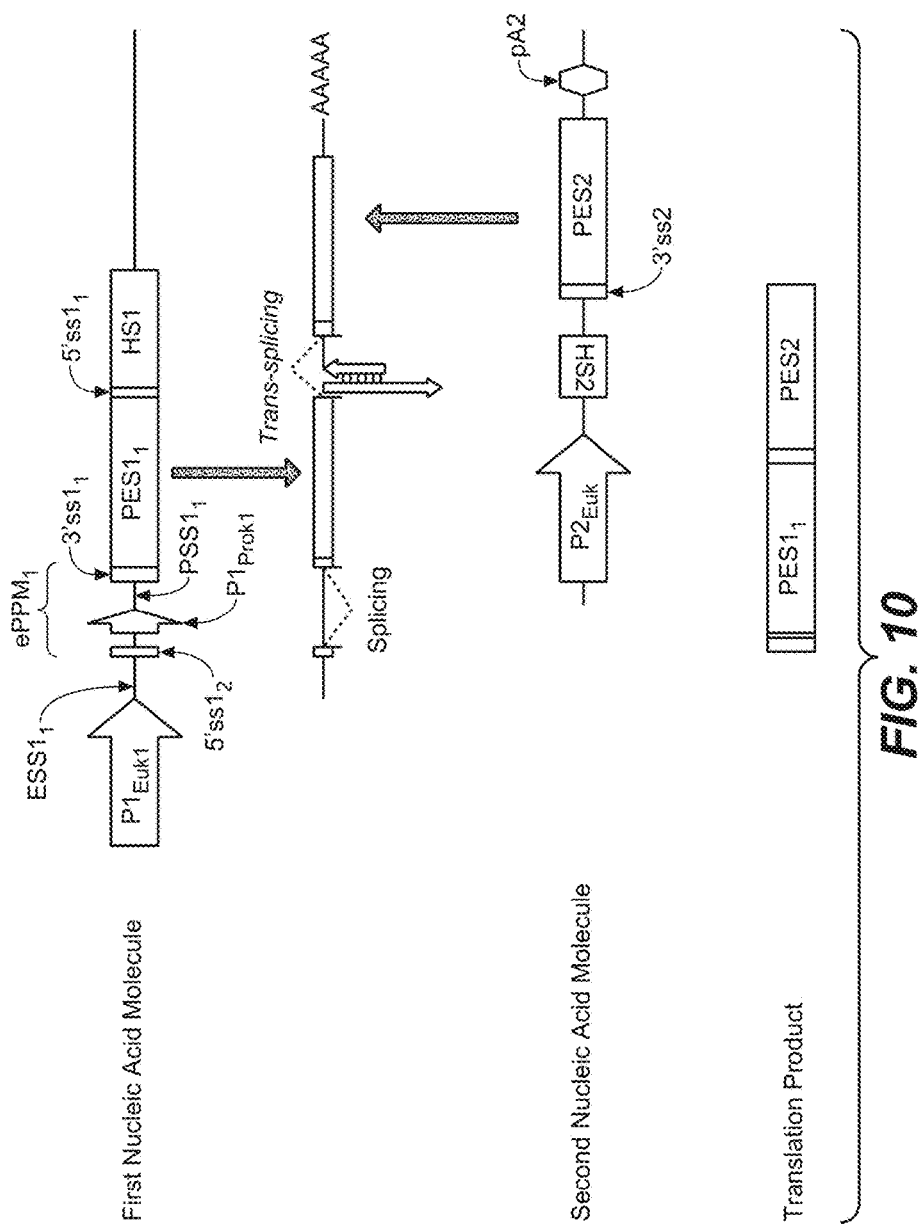
FIG. 10 is a schematic diagram showing the relative organization of possible first and second nucleic acid molecules for the general modular expression of a polypeptide product. The diagram also shows the general pre-mRNA products following transcription of the nucleic acid molecules in a eukaryotic cell, the expected trans-splicing event between two generated pre-mRNA products, and the resultant products following translation of the spliced mRNA molecules.

The polypeptide expression systems generated and characterized in Examples 1 and 2 demonstrate that modular, flexible polypeptide expression of any desired protein can be directly achieved by use of a polypeptide expression system, such as the optimized expression systems described above for protein reformatting in the context of phage display. Accordingly, the expression system will include two nucleic acid molecule components (polypeptide-encoding sequences $PES1_1$ and PES2) that each encodes a portion of a single desired polypeptide product, wherein these split coding regions of the protein are precisely joined together in vivo through pre-mRNA trans-splicing without the need for subcloning of the protein-encoding nucleic acid. As shown in FIG. 10, the first nucleic acid molecule includes an expression cassette having the $PES1_1$ and also includes a eukaryotic promoter ($P1_{Euk1}$) and a eukaryotic signal sequence ($ESS1_1$) upstream of the $PES1_1$ component, as well as a 5' splice site ($5'ss1_1$) and a hybridizing sequence (HS1) located downstream of $PES1_1$. The complementing, second nucleic acid molecule would include also include a eukaryotic promoter ($P2_{Euk}$), as well as a hybridizing sequence capable of hybridizing to HS1 (HS2) and a 3' splice site (3'ss2) upstream of the PES2 component. In addition, the second nucleic acid molecule would include a polyadenylation site (pA2) downstream of the PES2 component. Thus, when transcribed in a mammalian cell, the two generated pre-mRNA molecules, one with a lone 5'ss and the other with a lone 3'ss, would be directed together by their complementary hybridizing sequences (HS1 and HS2) and undergo trans-splicing to form a single, contiguous mRNA capable of subsequent translation and encoding the desired protein product.

The first nucleic acid molecule may further include an excisable prokaryotic promoter module ($ePPM_1$) that is positioned between the $P1_{Euk1}$ and the $PES1_1$ if expression of the polypeptide product encoded by $PES1_1$, and optionally the HS1 region, in prokaryotic cells is also desirable. The $ePPM_1$ may include a 5' splice site ($5'ss1_2$), a prokaryotic promoter ($P1_{Prok1}$), a first nucleic acid sequence encoding a prokaryotic signal sequence ($PSS1_1$), and a 3' splice site ($3'ss1_1$), operably linked to each other in a 5'-to-3' direction as $5'ss1_2$-$P1_{Prok1}$-$PSS1_1$-$3'ss1_1$. The $ePPM_1$ would drive the transcription of the encoded polypeptide of the first nucleic acid molecule in a prokaryotic cell. On the other hand, in a eukaryotic cell (e.g., mammalian cell), the P1$_{Euk1}$ would drive expression of the transcription of the encoded polypeptide of the first nucleic acid molecule, and the ePPM$_1$ would be removed from the pre-mRNA transcript by cis-splicing by virtue of hits flanking 5'ss1$_2$ and 3'ss1$_1$ components.

Figure 11:
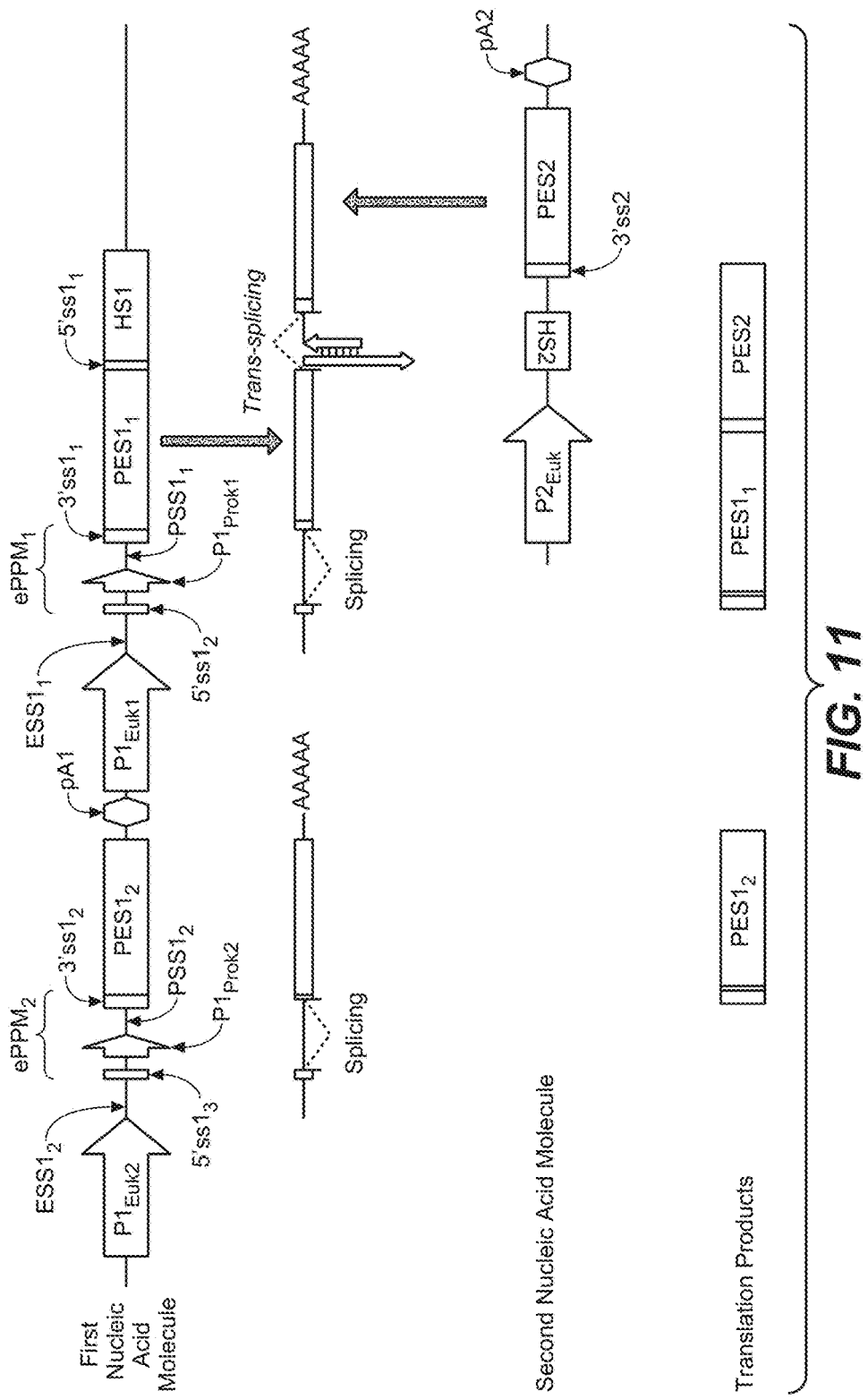
FIG. 11 is a schematic diagram showing the relative organization of possible first and second nucleic acid molecules for the general modular expression of more than one polypeptide products. The diagram also shows the general pre-mRNA products following transcription of the nucleic acid molecules in a eukaryotic cell, the expected transsplicing event between two generated pre-mRNA products, and the resultant products following translation of the spliced mRNA molecules.

In some instances, it may be desirable to also express a second polypeptide. The first nucleic acid molecule of the modular protein expression system may be accordingly designed to include a second expression cassette. As shown in FIG. 11, the second expression cassette encoding the second protein product (PES1$_2$) would be designed in a manner similar to the first expression cassette, but would contain a polyadenylation site (pA1) downstream of the PES1$_2$ sequence to ensure the generation of a distinct pre-mRNA molecule following transcription. In other instances, the second expression cassette could be designed into the second nucleic acid molecule of the polypeptide expression system.

Other Embodiments

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

What is claimed is:

1. A polypeptide expression system comprising a first nucleic acid molecule and a second nucleic acid molecule, wherein:
(a) the first nucleic acid molecule comprises a first expression cassette comprising the following components: (i) a first eukaryotic promoter ($P1_{Euk1}$), (ii) a prokaryotic promoter ($P1_{Prok1}$), (iii) a first polypeptide-encoding sequence ($PES1_1$), (iv) a first 5' splice site ($5'ss1_1$), (v) a hybridizing sequence (HS1), wherein the components are operably linked to each other in a 5'-to-3' direction as $P1_{Euk1}$-$P1_{Prok1}$-$PES1_1$-$5'ss1_1$-HS1, wherein the HS1 is a gene encoding all or a portion of a pill coat protein of bacteriophage M13, and wherein the HS1 comprises a mutated polyadenylation site; and
(b) the second nucleic acid molecule comprises the following components: (i) a eukaryotic promoter ($P2_{Euk}$), (ii) a hybridizing sequence capable of hybridizing to HS1 (HS2), (iii) a 3' splice site (3'ss2), (iv) a second polypeptide-encoding sequence (PES2), and (v) a polyadenylation site (pA2), wherein the components are operably linked to each other in a 5'-to-3' direction as $P2_{Euk}$-HS2-3'ss2-PES2-pA2.

2. The polypeptide expression system of claim 1, wherein the $P1_{Euk1}$ is a cytomegalovirus (CMV) promoter or a simian virus 40 (SV40) promoter.

3. The polypeptide expression system of claim 1, wherein the $P2_{Euk}$ is a CMV promoter or an SV40 promoter.

4. The polypeptide expression system of claim 1, wherein the first expression cassette further comprises a first nucleic acid sequence encoding a eukaryotic signal sequence (ESS1$_1$), wherein the ESS1$_1$ is positioned between the P1$_{Euk1}$ and the PES1$_1$.

5. The polypeptide expression system of claim 4, wherein the ESS1$_1$ is a variable heavy chain (VH) signal sequence.

6. The polypeptide expression system of claim 1, wherein the first expression cassette further comprises an excisable prokaryotic promoter module (ePPM1) comprising the following components: (i) a 5' splice site (5'ss1$_2$), (ii) the prokaryotic promoter (P1$_{Prok1}$, and (iii) a 3' splice site (3'ss1$_1$), wherein the components are operably linked to each other in a 5'-to-3' direction as 5'ss1$_2$-P1$_{Prok1}$-3'ss1$_1$, and wherein the ePPM$_1$ is positioned between the P1$_{Euk1}$ and the PES1$_1$.

7. The polypeptide expression system of claim 6, wherein the P1$_{Prok1}$ is a selected from the group consisting of a PhoA promoter, a Tac promoter, a Lac, and a Tphac promoter.

8. The polypeptide expression system of claim 6, wherein the ePPM$_1$, further comprises a first nucleic acid sequence encoding a prokaryotic signal sequence (PSS1$_1$).

9. The polypeptide expression system of claim 8, wherein the PSS1$_1$ is a heat-stable enterotoxin II (stII) signal sequence.

10. The polypeptide expression system of claim 8, further comprising a polypyrimidine tract positioned between the PSS1$_1$ and the 3'ss1$_1$ (PPT1$_1$).

11. The polypeptide expression system of claim 1, wherein the PES1$_1$ does not comprise a cryptic 5' splice site.

12. The polypeptide expression system of claim 1, wherein the first nucleic acid molecule further comprises a second expression cassette comprising (i) a second eukaryotic promoter (P1$_{Euk2}$), (ii) a second polypeptide-encoding sequence (PES1$_2$), and (iii) a polyadenylation site (pA1), wherein the components are operably linked to each other in a 5'-to-3' direction as P1$_{Euk2}$-PES1$_2$-pA1.

13. The polypeptide expression system of claim 12, wherein the P1$_{Euk2}$ is a CMV promoter or an SV40 promoter.

14. The polypeptide expression system of claim 12, wherein the second expression cassette further comprises a nucleic acid sequence encoding a eukaryotic signal sequence (ESS1$_2$).

15. The polypeptide expression system of claim 14, wherein the ESS1$_2$ is the murine binding immunoglobulin protein (mBiP) signal sequence.

16. The polypeptide expression system of claim 12, wherein the second expression cassette further comprises an excisable prokaryotic promoter module (ePPM$_2$) comprising the following components: (i) a 5' splice site (5'ss1$_3$), (ii) a prokaryotic promoter (P1$_{Prok2}$), and (iii) a 3' splice site (3'ss1$_2$), wherein the components are operably linked to each other in a 5'-to-3' direction as 5'ss1$_3$-P1$_{Prok2}$-3'ss1$_2$, and wherein the ePPM$_2$ is positioned between the P1$_{Euk2}$ and the PES1$_2$.

17. The polypeptide expression system of claim 16, wherein the P1$_{Prok2}$ is a selected from the group consisting of a PhoA promoter, a Tac promoter, and a Lac promoter.

18. The polypeptide expression system of claim 16, wherein the ePPM$_2$ further comprises a nucleic acid sequence encoding a prokaryotic signal sequence (PSS1$_2$).

19. The polypeptide expression system of claim 18, wherein the PSS1$_2$ is a heat-stable enterotoxin II (stII) signal sequence.

20. The polypeptide expression system of claim 18, further comprising a polypyrimidine tract positioned between the PSS1$_2$ and the 3'ss1$_2$ (PPT1$_2$).

21. The polypeptide expression system of claim 12, wherein the second expression cassette is positioned 5' to the first expression cassette.

22. The polypeptide expression system of claim 12, wherein the PES1$_2$ encodes all or a portion of an antibody.

23. The polypeptide expression system of claim 1, further comprising an intronic splice enhancer (ISE) positioned between the 5'ss1$_1$ and the HS1 (ISE1).

24. The polypeptide expression system of claim 23, wherein the ISE1 comprises a G-run comprising three or more consecutive guanine residues.

25. The polypeptide expression system of claim 23, further comprising a polypyrimidine tract positioned between the HS2 and the 3'ss2 (PPT2).

26. The polypeptide expression system of claim 25, further comprising an ISE positioned between the HS2 and the 3'ss2 (ISE2).

27. The polypeptide expression system of claim 26, wherein the ISE2 comprises a G-run comprising three or more consecutive guanine residues.

28. The polypeptide expression system of claim 1, wherein the PES1$_1$ encodes all or a portion of an antibody.

29. The polypeptide expression system of claim 28, wherein the PES1$_1$ encodes a polypeptide comprising a VH domain.

30. The polypeptide expression system of claim 29, wherein the polypeptide comprising the VH domain further comprises a CH1 domain.

31. The polypeptide expression system of claim 28, wherein the PES2 encodes all or a portion of an antibody.

32. The polypeptide expression system of claim 1, wherein the mutated polyadenylation site comprises one or more silent mutations.

33. A vector set comprising a first vector and a second vector, wherein the first and second vectors comprise the first and second nucleic acid molecules, respectively, of the polypeptide expression system of claim 1.

34. A nucleic acid molecule comprising a set of splice sites consisting of a first 5' splice site (5'ss1$_1$), a second 5' splice site (5'ss1$_2$), and a 3' splice site (3'ss1$_1$), the nucleic acid comprising a first expression cassette, the first expression cassette comprising the following components:
  (a) a first eukaryotic promoter (P1$_{Euk1}$);
  (b) a first excisable prokaryotic promoter module (ePPM$_1$) comprising the following components:
    (i) the 5'ss1$_2$;
    (ii) a prokaryotic promoter (P1$_{Prok1}$); and
    (iii) the 3'ss1$_1$,
    wherein the components of the ePPM$_1$ are operably linked to each other in a 5'-to-3' direction as 5'ss1$_2$-P1$_{Prok1}$-3'ss1$_1$;
  (c) a first polypeptide-encoding sequence (PES1$_1$);
  (d) the 5'ss1$_1$; and
  (e) a utility peptide-encoding sequence (UPES), wherein the UPES encodes all or a portion of a pill coat protein of bacteriophage M13, and wherein the UPES comprises a mutated polyadenylation site,
  wherein the components of the first expression cassette are operably linked to each other in a 5'-to-3' direction as P1$_{Euk1}$-ePPM$_1$-PES1$_1$-5'ss1$_1$-UPES.

35. The nucleic acid molecule of claim 34, wherein the first expression cassette further comprises a first nucleic acid sequence encoding a eukaryotic signal sequence (ESS1$_1$), wherein the ESS1$_1$ is positioned between the P1$_{Euk1}$ and the ePPM$_1$.

36. The nucleic acid molecule of claim 34, wherein the ePPM$_1$ further comprises a first nucleic acid sequence encoding a prokaryotic signal sequence (PSS1$_1$), wherein the PSS1$_1$ is positioned between the P1$_{Prok1}$ and the 3'ss1$_1$.

37. A vector comprising the nucleic acid molecule of claim 34.

38. A host cell comprising the vector of claim 37 or the vector set of claim 33.

39. The host cell of claim 38, wherein the host cell is a prokaryotic cell.

40. The host cell of claim 38, wherein the host cell is a eukaryotic cell.

41. A method for producing a polypeptide comprising the amino acid sequence encoded by the PES1$_1$, the method comprising culturing a host cell that comprises the vector of claim 37 in a culture medium.

42. The method of claim 41, wherein the method further comprises recovering the polypeptide from the host cell or the culture medium.

43. A method for producing a polypeptide comprising the amino acid sequence encoded by the PES1 and the amino acid sequence encoded by the PES2, the method comprising culturing a host cell that comprises the vector set of claim 33 in a culture medium.

44. The method of claim 43, wherein the method further comprises recovering the polypeptide from the host cell or the culture medium.

45. A nucleic acid molecule comprising a set of splice sites consisting of a first 5' splice site (5'ss1$_1$), a second 5' splice site (5'ss1$_2$), a third 5' splice site (5'ss1$_3$), a first 3' splice site (3'ss1$_1$), and a second 3' splice site (3'ss1$_2$), wherein the nucleic acid molecule comprises:
(a) a first expression cassette, the first expression cassette comprising the following components:
  (i) a first eukaryotic promoter (P1$_{Euk1}$);
  (ii) a first excisable prokaryotic promoter module (ePPM$_1$) comprising the 5'ss1$_2$, a prokaryotic promoter (P1$_{Prok1}$), and the 3'ss1$_1$, wherein the components of the ePPM$_1$ are operably linked to each other in a 5'-to-3' direction as 5'ss1$_2$-P1$_{Prok1}$-3'ss1$_1$;
  (iii) a first polypeptide-encoding sequence (PES1$_1$);
  (iv) the 5'ss1$_1$; and
  (v) a utility peptide-encoding sequence (UPES), wherein the UPES encodes all or a portion of a pill coat protein of bacteriophage M13, and wherein the UPES comprises a mutated polyadenylation site, and
(b) a second expression cassette, the second expression cassette comprising the following components:
  (i) a second eukaryotic promoter (P1$_{Euk2}$);
  (ii) a second excisable prokaryotic promoter module (ePPM$_2$) comprising the 5'ss1$_3$, a prokaryotic promoter (P1$_{Prok2}$), and the 3'ss1$_2$, wherein the components of the ePPM$_2$ are operatively linked to each other in a 5'-to-3' direction as 5'ss1$_3$-P1$_{Prok2}$-3'ss1$_2$;
  (iii) a second polypeptide-encoding sequence (PES1$_2$); and
  (iv) a polyadenylation site (pA1),
wherein the components are operably linked to each other in a 5'-to-3' direction as P1$_{Euk2}$-ePPM$_2$-PES1$_2$-pA1-P1$_{Euk1}$-ePPM$_1$-PES1$_1$-5'ss1$_1$-UPES.

46. The nucleic acid molecule of claim 45, wherein the second expression cassette further comprises a second nucleic acid sequence encoding a eukaryotic signal sequence (ESS1$_2$), wherein the ESS1$_2$ is positioned between the P1$_{Euk2}$ and the PES1$_2$.

47. The nucleic acid molecule of claim 45, wherein the ePPM$_2$ further comprises a nucleic acid sequence encoding a prokaryotic signal sequence (PSS1$_2$), wherein the PSS1$_2$ is positioned between the P1$_{Prok2}$ and the 3'ss1$_2$.

* * * * *

UNITED STATES PATENT AND TRADEMARK OFFICE
CERTIFICATE OF CORRECTION

PATENT NO. : 10,308,944 B2
APPLICATION NO. : 14/790818
DATED : June 4, 2019
INVENTOR(S) : Isidro Hotzel et al.

It is certified that error appears in the above-identified patent and that said Letters Patent is hereby corrected as shown below:

In the Specification

Column 2, Line 26, replace "the pill protein" with --the pIII protein--;
Line 27, replace "the pill fragment" with --the pIII fragment--;
Line 28, replace "the pill protein" with --the pIII protein--;
Line 29, replace "the pill protein" with --the pIII protein--.

Column 4, Line 16, replace "the pill of" with --the pIII of--.

Column 5, Line 9, replace "(in g/ml)" with --(in μg/ml)--;
Line 12, replace "(in g/ml)" with --(in μg/ml)--;

Column 6, Line 31, replace "anti-M13 $p^3$" with --anti-M13 p3--.

Column 8, Line 6, replace "and a classes" with --and α classes--.

Column 9, Line 56, replace "may be the pill" with --may be the pIII--;
Line 58, replace "bacteriophage pill" with --bacteriophage pIII--;
Line 61, replace "the pill sequence" with --the pIII sequence--.

Column 10, Line 9, replace "the pill fragment" with --the pIII fragment--.

Column 13, Line 56, replace "portion of the pill" with --portion of the pIII--;
Line 57, replace "a pill fragment" with --a pIII fragment--;
Line 58, replace "the pill protein" with --the pIII protein--;
Line 59, replace "the pill protein" with --the pIII protein--;
Line 60, replace "fragment-pill protein" with --fragment-pIII protein--.

Column 15, Line 19, replace "(PSS1)" with --($PSS1_1$)--;
Line 37, replace "TTCCTTTTTTTCTCTTTCC" with --TTCCTTTTTCTCTTTCC--;

Signed and Sealed this
Fourth Day of May, 2021

Drew Hirshfeld
*Performing the Functions and Duties of the*
*Under Secretary of Commerce for Intellectual Property and*
*Director of the United States Patent and Trademark Office*

CERTIFICATE OF CORRECTION (continued)
U.S. Pat. No. 10,308,944 B2

Line 58, replace "-P1$_{Prok2}$, PSS1$_2$" with -- -P1$_{Prok2}$-PSS1$_2$--.

Column 17, Line 35, replace "to pill of M13" with --to pIII of M13--.

Column 25, Line 55, replace "bacteriophage pill coat" with --bacteriophage pIII coat--.

Column 26, Line 8, replace "up to 25 g/ml" with --up to 25 µg/ml--.

In the Claims

Column 49, Line 65, Claim 1 replace "a pill coat protein" with --a pIII coat protein--.

Column 52, Line 55, Claim 34 replace "a pill coat protein" with --a pIII coat protein--.

Column 54, Line 7, Claim 45 replace "of a pill" with --of a pIII--.

SEQUENCE LISTING

<160> NUMBER OF SEQ ID NOS: 31

<210> SEQ ID NO 1
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
ttcctttttt ctctttcc                                                     18

<210> SEQ ID NO 2
<211> LENGTH: 400
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2
gccaccatga tgaaatttac cgtggtggcg gcggcgctgc tgctgctggg cggtaagtac        60
cgcctataga gtctataggc ccaccccctt ggcttacgta aagaagttat tgaagcatcc       120
tcgtcagtaa aaagttaatc ttttcaacag ctgtcataaa gttgtcacgg ccgagactta       180
tagtcgcttt gttttatt ttttatgtat ttgtaactag tacgcaagtt cacgtaaaaa        240
gggtatgtag aggttgaggt gattttatga aaaagaatat cgcatttctt cttgcatcta       300
tgttcctttt ttctctttcc acagccgtac gcgcagatat ccagatgacc cagtccccga       360
gctccctgtc cgcctctgtg ggcgataggg tcaccatcac                             400

<210> SEQ ID NO 3
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Met Met Lys Phe Thr Val Val Ala Ala Ala Leu Leu Leu Leu
1               5                   10

<210> SEQ ID NO 4
<211> LENGTH: 37
<212> TYPE: PRT

<213> ORGANISM: Artificial Sequence
<220> FEATURE:
<223> OTHER INFORMATION: Description of Artificial Sequence: Synthetic
      polypeptide

<400> SEQUENCE: 4

Ala Ser Ile Ala Arg Leu Glu Glu Lys Val Lys Thr Leu Lys Ala Gln
1               5                   10                  15

Asn Tyr Glu Leu Ala Ser Thr Ala Asn Met Leu Arg Glu Gln Val Ala
            20                  25                  30

Gln Leu Gly Gly Cys
        35

<210> SEQ ID NO 5
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Ala Ser Ile Asp Glu Leu Gln Ala Glu Val Glu Gln Leu Glu Glu Arg
1               5                   10                  15

Asn Tyr Ala Leu Arg Lys Glu Val Glu Asp Leu Gln Lys Gln Ala Glu
            20                  25                  30

Lys Leu Gly Gly Cys
        35

<210> SEQ ID NO 6
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(6)
<223> OTHER INFORMATION: a, c, t, g, unknown or other
<220> FEATURE:
<221> NAME/KEY: modified_base
<222> LOCATION: (9)..(9)
<223> OTHER INFORMATION: a, c, t, g, unknown or other
<220> FEATURE:
<221> NAME/KEY: modified_base
<222> LOCATION: (12)..(12)
<223> OTHER INFORMATION: a, c, t, g, unknown or other
<220> FEATURE:
<221> NAME/KEY: modified_base
<222> LOCATION: (15)..(15)
<223> OTHER INFORMATION: a, c, t, g, unknown or other
<220> FEATURE:
<221> NAME/KEY: modified_base
<222> LOCATION: (18)..(18)
<223> OTHER INFORMATION: a, c, t, g, unknown or other
<220> FEATURE:
<221> NAME/KEY: modified_base
<222> LOCATION: (21)..(21)
<223> OTHER INFORMATION: a, c, t, g, unknown or other
<220> FEATURE:
<221> NAME/KEY: modified_base
<222> LOCATION: (24)..(24)
<223> OTHER INFORMATION: a, c, t, g, unknown or other
<220> FEATURE:
<221> NAME/KEY: modified_base
<222> LOCATION: (27)..(27)
<223> OTHER INFORMATION: a, c, t, g, unknown or other
<220> FEATURE:
<221> NAME/KEY: modified_base
<222> LOCATION: (30)..(30)

```
<223> OTHER INFORMATION: a, c, t, g, unknown or other
<220> FEATURE:
<221> NAME/KEY: modified_base
<222> LOCATION: (33)..(33)
<223> OTHER INFORMATION: a, c, t, g, unknown or other
<220> FEATURE:
<221> NAME/KEY: modified_base
<222> LOCATION: (36)..(36)
<223> OTHER INFORMATION: a, c, t, g, unknown or other
<220> FEATURE:
<221> NAME/KEY: modified_base
<222> LOCATION: (39)..(39)
<223> OTHER INFORMATION: a, c, t, g, unknown or other
<220> FEATURE:
<221> NAME/KEY: modified_base
<222> LOCATION: (42)..(42)
<223> OTHER INFORMATION: a, c, t, g, unknown or other

<400> SEQUENCE: 6
atgaanttna cngtngtngc ngcngcnctn ctnctnctng gn                          42

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
ttcctctttc cctttctctc c                                                 21

<210> SEQ ID NO 8
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8 gtaaga                                                                   6

<210> SEQ ID NO 9
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Met Lys Lys Asn Ile Ala Phe Leu Leu Ala Ser Met Phe Leu Phe Ser
1               5                   10                  15

Leu Ser Thr Ala Val Arg Ala Asp Ile Gln Met Thr Gln Ser Pro Ser
            20                  25                  30

Ser Leu Ser Ala Ser Val Gly Asp Arg Val Thr Ile Thr
        35                  40                  45

<210> SEQ ID NO 10
<211> LENGTH: 400
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 10
```

-continued

```
gccaccatgg atggtcatg tatcatcctt tttctagtag caactgcaac aggtaagtac    60
cgcctataga gtctataggc ccaccccctt ggcttacgta aagaagttat tgaagcatcc   120
tcgtcagtaa aaagttaatc ttttcaacag ctgtcataaa gttgtcacgg ccgagactta   180
tagtcgcttt gttttatttt ttttatcatc gtggccctag tacgcaaatt cacgtaaaaa   240
gggtaactag aggttgaggt gattttatga aaaagaatat cgcatttctt cttgcatcta   300
tgttcctttt ttctctttcc acagcggtcc gcgcagaagt tcagctggtg gagtctggcg   360
gtggcctggt gcagccaggg ggctcactcc gtttgtcctg                         400
```

<210> SEQ ID NO 11
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Ala Ser Ile Ala Arg Leu Arg Glu Arg Val Lys Thr Leu Arg Ala Arg
1               5                   10                  15

Asn Tyr Glu Leu Arg Ser Arg Ala Asn Met Leu Arg Glu Arg Val Ala
            20                  25                  30

Gln Leu Gly Gly Cys
        35

<210> SEQ ID NO 12
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Ala Ser Leu Asp Glu Leu Glu Ala Glu Ile Glu Gln Leu Glu Glu Glu
1               5                   10                  15

Asn Tyr Ala Leu Glu Lys Glu Ile Glu Asp Leu Glu Lys Glu Leu Glu
            20                  25                  30

Lys Leu Gly Gly Cys
        35

<210> SEQ ID NO 13
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Glu Glu Lys Ser Arg Leu Leu Glu Lys Glu Asn Arg Glu Leu Glu Lys
1               5                   10                  15

Ile Ile Ala Glu Lys Glu Glu Arg Val Ser Glu Leu Arg His Gln Leu
            20                  25                  30

Gln Ser Val Gly Gly Cys
        35

<210> SEQ ID NO 14
<211> LENGTH: 38
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 14

Thr Ser Arg Leu Glu Gly Leu Gln Ser Glu Asn His Arg Leu Arg Met
1               5                   10                  15

Lys Ile Thr Glu Leu Asp Lys Asp Leu Glu Val Thr Met Gln Leu
            20                  25                  30

Gln Asp Val Gly Gly Cys
        35

<210> SEQ ID NO 15
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Ala Gly Ser Cys
1

<210> SEQ ID NO 16
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Cys Pro Pro Cys Pro Gly
1               5

<210> SEQ ID NO 17
<211> LENGTH: 418
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Ala Glu Asp Ile Glu Phe Ala Ser Gly Gly Ser Gly Ala Glu Thr
1               5                   10                  15

Val Glu Ser Cys Leu Ala Lys Pro His Thr Glu Asn Ser Phe Thr Asn
            20                  25                  30

Val Trp Lys Asp Asp Lys Thr Leu Asp Arg Tyr Ala Asn Tyr Glu Gly
        35                  40                  45

Cys Leu Trp Asn Ala Thr Gly Val Val Val Cys Thr Gly Asp Glu Thr
    50                  55                  60

Gln Cys Tyr Gly Thr Trp Val Pro Ile Gly Leu Ala Ile Pro Glu Asn
65                  70                  75                  80

Glu Gly Gly Gly Ser Glu Gly Gly Ser Glu Gly Gly Ser Glu
                85                  90                  95

Gly Gly Gly Thr Lys Pro Pro Glu Tyr Gly Asp Thr Pro Ile Pro Gly
            100                 105                 110

Tyr Thr Tyr Ile Asn Pro Leu Asp Gly Thr Tyr Pro Pro Gly Thr Glu
        115                 120                 125

Gln Asn Pro Ala Asn Pro Asn Pro Ser Leu Glu Glu Ser Gln Pro Leu
```

```
                130                 135                 140
Asn Thr Phe Met Phe Gln Asn Arg Phe Arg Asn Arg Gln Gly Ala
145                 150                 155                 160

Leu Thr Val Tyr Thr Gly Thr Val Thr Gln Gly Thr Asp Pro Val Lys
                165                 170                 175

Thr Tyr Tyr Gln Tyr Thr Pro Val Ser Ser Lys Ala Met Tyr Asp Ala
                180                 185                 190

Tyr Trp Asn Gly Lys Phe Arg Asp Cys Ala Phe His Ser Gly Phe Asn
            195                 200                 205

Glu Asp Pro Phe Val Cys Glu Tyr Gln Gly Gln Ser Ser Asp Leu Pro
        210                 215                 220

Gln Pro Pro Val Asn Ala Gly Gly Ser Gly Gly Ser Gly Gly
225                 230                 235                 240

Gly Ser Glu Gly Gly Gly Ser Glu Gly Gly Ser Glu Gly Gly Gly
                245                 250                 255

Ser Glu Gly Gly Gly Ser Gly Gly Ser Gly Ser Gly Asp Phe Asp
            260                 265                 270

Tyr Glu Lys Met Ala Asn Ala Asn Lys Gly Ala Met Thr Glu Asn Ala
        275                 280                 285

Asp Glu Asn Ala Leu Gln Ser Asp Ala Lys Gly Lys Leu Asp Ser Val
290                 295                 300

Ala Thr Asp Tyr Gly Ala Ala Ile Asp Gly Phe Ile Gly Asp Val Ser
305                 310                 315                 320

Gly Leu Ala Asn Gly Asn Gly Ala Thr Gly Asp Phe Ala Gly Ser Asn
                325                 330                 335

Ser Gln Met Ala Val Gly Asp Gly Asp Asn Ser Pro Leu Met Asn Asn
            340                 345                 350

Phe Arg Gln Tyr Leu Pro Ser Leu Pro Gln Ser Val Glu Cys Arg Pro
        355                 360                 365

Phe Val Phe Ser Ala Gly Lys Pro Tyr Glu Phe Ser Ile Asp Cys Asp
    370                 375                 380

Lys Ile Asn Leu Phe Arg Gly Val Phe Ala Phe Leu Leu Tyr Val Ala
385                 390                 395                 400

Thr Phe Met Tyr Val Phe Ser Thr Phe Ala Asn Ile Leu Arg Asn Lys
                405                 410                 415

Glu Ser

<210> SEQ ID NO 18
<211> LENGTH: 158
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Ser Gly Gly Gly Ser Gly Ser Gly Asp Phe Asp Tyr Glu Lys Met Ala
1               5                   10                  15

Asn Ala Asn Lys Gly Ala Met Thr Glu Asn Ala Asp Glu Asn Ala Leu
            20                  25                  30

Gln Ser Asp Ala Lys Gly Lys Leu Asp Ser Val Ala Thr Asp Tyr Gly
        35                  40                  45

Ala Ala Ile Asp Gly Phe Ile Gly Asp Val Ser Gly Leu Ala Asn Gly
    50                  55                  60

Asn Gly Ala Thr Gly Asp Phe Ala Gly Ser Asn Ser Gln Met Ala Gln
```

```
                 65                  70                  75                  80
Val Gly Asp Gly Asp Asn Ser Pro Leu Met Asn Asn Phe Arg Gln Tyr
                         85                  90                  95

Leu Pro Ser Leu Pro Gln Ser Val Glu Cys Arg Pro Phe Val Phe Gly
                100                 105                 110

Ala Gly Lys Pro Tyr Glu Phe Ser Ile Asp Cys Asp Lys Ile Asn Leu
            115                 120                 125

Phe Arg Gly Val Phe Ala Phe Leu Leu Tyr Val Ala Thr Phe Met Tyr
        130                 135                 140

Val Phe Ser Thr Phe Ala Asn Ile Leu Arg Asn Lys Glu Ser
145                 150                 155

<210> SEQ ID NO 19
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Met Gly Trp Ser Cys Ile Ile Leu Phe Leu Val Ala Thr Ala Thr
1               5                   10                  15

<210> SEQ ID NO 20
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Met Lys Lys Asn Ile Ala Phe Leu Leu Ala Ser Met Phe Leu Phe Ser
1               5                   10                  15

Leu Ser Thr Ala Val Arg Ala Glu Val Gln Leu Val Glu Ser Gly Gly
            20                  25                  30

Gly Leu Val Gln Pro Gly Gly Ser Leu Arg Leu Ser Cys
        35                  40                  45

<210> SEQ ID NO 21
<211> LENGTH: 600
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 21
cacaagccca gcaacaccaa ggtcgacaag aaagtaggta agaaatcttg tgacaaaact      60
cacacatgcg ccggccctc tggttccggt gattttgatt atgaaaagat ggcaaacgct     120
aataaggggg ctatgaccga aaatgccgat gaaaacgcgc tacagtctga cgctaaaggc    180
aaacttgatt ctgtcgctac tgattacggt gctgctatcg atggtttcat tggtgacgtt    240
tccggccttg ctaatggtaa tggtgctact ggtgattttg ctggctctaa ttcccaaatg    300
gctcaagtcg gtgacggtga taattcacct ttaatgaata atttccgtca atatttacct    360
tccctccctc aatcggttga atgtcgccct tttgtcttta gcgctggtaa accatatgaa    420
ttttctattg attgtgacaa gattaactta ttccgtggtg tctttgcgtt ctcttttatat    480 gttgccacct ttatgtatgt attttctacg tttgctaaca tactgcgtaa taaggagtct    540
```
taaccgtggg gtgaacgctc ggttgccgcc gggcgttttt tatgttcttt tggaggatcc    600

<210> SEQ ID NO 22
<211> LENGTH: 180
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

His Lys Pro Ser Asn Thr Lys Val Asp Lys Lys Val Gly Lys Lys Ser
1               5                   10                  15

Cys Asp Lys Thr His Thr Cys Gly Arg Pro Ser Gly Ser Gly Asp Phe
            20                  25                  30

Asp Tyr Glu Lys Met Ala Asn Ala Asn Lys Gly Ala Met Thr Glu Asn
        35                  40                  45

Ala Asp Glu Asn Ala Leu Gln Ser Asp Ala Lys Gly Lys Leu Asp Ser
    50                  55                  60

Val Ala Thr Asp Tyr Gly Ala Ala Ile Asp Gly Phe Ile Gly Asp Val
65                  70                  75                  80

Ser Gly Leu Ala Asn Gly Asn Gly Ala Thr Gly Asp Phe Ala Gly Ser
                85                  90                  95

Asn Ser Gln Met Ala Gln Val Gly Asp Gly Asp Asn Ser Pro Leu Met
            100                 105                 110

Asn Asn Phe Arg Gln Tyr Leu Pro Ser Leu Pro Gln Ser Val Glu Cys
        115                 120                 125

Arg Pro Phe Val Phe Ser Ala Gly Lys Pro Tyr Glu Phe Ser Ile Asp
    130                 135                 140

Cys Asp Lys Ile Asn Leu Phe Arg Gly Val Phe Ala Phe Leu Leu Tyr
145                 150                 155                 160

Val Ala Thr Phe Met Tyr Val Phe Ser Thr Phe Ala Asn Ile Leu Arg
                165                 170                 175

Asn Lys Glu Ser
            180

<210> SEQ ID NO 23
<211> LENGTH: 600
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 23
gtctatataa gcagagctcg tttagtgaac cgtcagatcg cctggagacg ccatccacgc    60
tgttttgacc tccatagaag acaccgggac cgatccagcc tccgcggccg ggaacggtgc    120
attggaacgc ggattccccg tgccaagagt gacgaacgtc accatgaaa ccatcgatag     180 cagcaccgta atcagtagcg acagaatcaa gtttgccttt agcgtcagac tgtagcgcgt    240
tttcatcggc attttcggtc atagcccct tattagcgtt tgccatcttt tcataatcaa     300
aatcccaccc ccttggcttc gttagtagac tagatctaat ctactctact aaccgcctat    360
agagtctata ggcccacccc cttggcttta ctgacacacg aattcctctt tccctttctc    420
tccacagagc ccaaatcttg tgacaaaact cacacatgcc caccgtgccc agcacctgaa    480
ctcctgggcg gaccgtcagt cttcctcttc cccccaaaac ccaaggacac cctcatgatc    540
tcccggaccc ctgaggtcac atgcgtggtg gtggacgtga gccacgaaga ccctgaggtc    600

<210> SEQ ID NO 24
<211> LENGTH: 58
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val
    50                  55

<210> SEQ ID NO 25
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Met Met Lys Phe Thr Val Val Ala Ala Ala Leu Leu Leu Leu Gly
1               5                   10                  15

<210> SEQ ID NO 26
<211> LENGTH: 600
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 26
gtggtgaccg tgccctccag cagcttgggc acccagacct acatctgcaa cgtgaatcac     60
aagcccagca acaccaaggt cgacaagaaa gtaggtaaga atcttgtgac aaaactcac    120 acatgcgggg gggggagtgg gagcggggat tttgattatg aaaagatggc aaacgctaat    180
aagggggcta tgaccgaaaa tgccgatgaa aacgcgctac agtctgacgc taaaggcaaa    240
cttgattctg tcgctactga ttacggtgct gctatcgatg gtttcattgg tgacgtttcc    300
ggccttgcta atggtaatgg tgctactggt gattttgctg ctctaattcc caaatggct    360 caagtcggtg acggtgataa ttcacccttta atgaataatt ccgtcaata tttaccttcc    420 ctccctcaat cggttgaatg tcgcccttttt gtcttttagcg ctggtaaaacc atatgaattt    480 tctattgatt gtgacaagat caacttattc cgtggtgtct ttgcgtttct tttatatgtt    540
gccaccttta tgtatgtatt ttctacgttt gctaacatac tgcgtaataa ggagtcttaa    600

<210> SEQ ID NO 27
<211> LENGTH: 199
<212> TYPE: PRT
<213> ORGANISM: Artificial Sequence
<220> FEATURE:
<223> OTHER INFORMATION: Description of Artificial Sequence: Synthetic
      polypeptide -continued

<400> SEQUENCE: 27

Val Val Thr Val Pro Ser Ser Leu Gly Thr Gln Thr Tyr Ile Cys
1               5                   10                  15

Asn Val Asn His Lys Pro Ser Asn Thr Lys Val Asp Lys Lys Val Gly
            20                  25                  30

Lys Lys Ser Cys Asp Lys Thr His Thr Cys Gly Gly Gly Ser Gly Ser
        35                  40                  45

Gly Asp Phe Asp Tyr Glu Lys Met Ala Asn Ala Asn Lys Gly Ala Met
    50                  55                  60

Thr Glu Asn Ala Asp Glu Asn Ala Leu Gln Ser Asp Ala Lys Gly Lys
65                  70                  75                  80

Leu Asp Ser Val Ala Thr Asp Tyr Gly Ala Ala Ile Asp Gly Phe Ile
                85                  90                  95

Gly Asp Val Ser Gly Leu Ala Asn Gly Asn Gly Ala Thr Gly Asp Phe
            100                 105                 110

Ala Gly Ser Asn Ser Gln Met Ala Gln Val Gly Asp Gly Asp Asn Ser
        115                 120                 125

Pro Leu Met Asn Asn Phe Arg Gln Tyr Leu Pro Ser Leu Pro Gln Ser
    130                 135                 140

Val Glu Cys Arg Pro Phe Val Phe Ser Ala Gly Lys Pro Tyr Glu Phe
145                 150                 155                 160

Ser Ile Asp Cys Asp Lys Ile Asn Leu Phe Arg Gly Val Phe Ala Phe
                165                 170                 175

Leu Leu Tyr Val Ala Thr Phe Met Tyr Val Phe Ser Thr Phe Ala Asn
            180                 185                 190

Ile Leu Arg Asn Lys Glu Ser
        195

<210> SEQ ID NO 28
<211> LENGTH: 600
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 28
gtctatataa gcagagctcg tttagtgaac cgtcagatcg cctggagacg ccatccacgc      60
tgttttgacc tccatagaag acaccgggac cgatccagcc tccgcggccg ggaacggtgc     120
attggaacgc ggattccccg tgccaagagt gacgaacgtc accaatgaaa ccatcgatag     180
cagcaccgta atcagtagcg acagaatcaa gtttgccttt agcgtcagac tgtagcgcgt     240
tttcatcggc attttcggtc atagccccct tattagcgtt tgccatcttt tcataatcaa     300
aatcccaccc ccttggcttc gttagtagac tagatctaat ctactctact aggggggggg     360
accgcctata gagtctatag gcccaccccc ttggctttac tgacacacga attcctcttt     420 cccttttctct ccacagagcc caaatcttgt gacaaaactc acacatgccc accgtgccca     480
gcacctgaac tcctgggcgg accgtcagtc ttcctcttcc ccccaaaacc caaggacacc     540
ctcatgatct cccggacccc tgaggtcaca tgcgtggtgg tggacgtgag ccacgaagac     600

<210> SEQ ID NO 29
<211> LENGTH: 55
<212> TYPE: PRT
<213> ORGANISM: Artificial Sequence
<220> FEATURE:
<223> OTHER INFORMATION: Description of Artificial Sequence: Synthetic

```
                  polypeptide

<400> SEQUENCE: 29

Glu Pro Lys Ser Cys Asp Lys Thr His Thr Cys Pro Pro Cys Pro Ala
1               5                  10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp
    50                  55

<210> SEQ ID NO 30
<211> LENGTH: 500
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 30
gtctatataa gcagagctcg tttagtgaac cgtcagatcg cctggagacg ccatccacgc     60
tgttttgacc tccatagaag acaccgggac cgatccagcc tccgcggccg ggaacggtgc    120
attggaacgc ggattccccg tgccaagagt gacgaacgtc accaatgaaa ccatcgatag    180
cagcaccgta atcagtagcg acagaatcaa gtttgccttt agcgtcagac tgtagcgcgt    240
tttcatcggc attttcggtc atagccccct tattagcgtt tgccatcttt tcataatcaa    300
aatcccaccc ccttggcttc gttagtagac tagatctaat ctactctact aggggggggg    360
accgcctata gagtctatag gcccacccccc ttggctttac tgacacacga attcctcttt    420 cccttctctct ccacagagcc caaatcttgt gacaaaactc acacagatta taaggacgat    480
gacgataaat gagtgcgacg                                                500

<210> SEQ ID NO 31
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Glu Pro Lys Ser Cys Asp Lys Thr His Thr Asp Tyr Lys Asp Asp Asp
1               5                  10                  15

Asp Lys
```